(12) United States Patent
Hughett

(10) Patent No.: US 7,585,304 B2
(45) Date of Patent: Sep. 8, 2009

(54) ENDOSCOPIC CLIP APPLYING APPARATUS WITH IMPROVED APERTURE FOR CLIP RELEASE AND RELATED METHOD

(75) Inventor: J. David Hughett, Wake Forest, NC (US)

(73) Assignee: Teleflex Medical Incorporated, Limerick, PA (US)

( * ) Notice: Subject to any disclaimer, the term of this patent is extended or adjusted under 35 U.S.C. 154(b) by 746 days.

(21) Appl. No.: 10/770,299

(22) Filed: Feb. 2, 2004

(65) Prior Publication Data

US 2005/0171560 A1 Aug. 4, 2005

(51) Int. Cl.
*A61B 17/10* (2006.01)
(52) U.S. Cl. ........................................ 606/142; 606/143
(58) Field of Classification Search ................. 606/138, 606/142, 144, 139, 143, 206–208
See application file for complete search history.

(56) References Cited

U.S. PATENT DOCUMENTS

| | | | | |
|---|---|---|---|---|
| 4,430,997 A * | 2/1984 | DiGiovanni et al. | ........ | 606/143 |
| 4,509,518 A | 4/1985 | McGarry et al. | ............ | 128/325 |
| 4,662,373 A | 5/1987 | Montgomery et al. | ....... | 128/325 |
| 5,049,152 A * | 9/1991 | Simon et al. | ................. | 606/143 |
| 5,084,057 A * | 1/1992 | Green et al. | ................. | 606/142 |
| 5,171,247 A * | 12/1992 | Hughett et al. | .............. | 606/142 |
| 5,197,970 A * | 3/1993 | Green et al. | ................. | 606/158 |
| 5,207,691 A | 5/1993 | Nardella | ..................... | 606/142 |
| 5,290,309 A * | 3/1994 | Kothe | ......................... | 606/207 |
| 5,409,498 A * | 4/1995 | Braddock et al. | ........... | 606/143 |
| 5,431,668 A * | 7/1995 | Burbank et al. | ............. | 606/143 |
| 5,527,318 A * | 6/1996 | McGarry | .................... | 606/139 |
| 5,573,541 A | 11/1996 | Green et al. | ................. | 606/143 |
| 5,681,330 A * | 10/1997 | Hughett et al. | .............. | 606/143 |
| 5,700,270 A * | 12/1997 | Peyser et al. | ................ | 606/142 |
| 5,700,271 A * | 12/1997 | Whitfield et al. | ............ | 606/143 |
| 5,755,726 A * | 5/1998 | Pratt et al. | ................... | 606/143 |
| 5,772,673 A * | 6/1998 | Cuny et al. | .................. | 606/142 |
| 5,792,150 A * | 8/1998 | Pratt et al. | ................... | 606/143 |
| 5,827,279 A * | 10/1998 | Hughett et al. | ................ | 606/45 |
| 5,833,700 A * | 11/1998 | Fogelberg et al. | ........... | 606/158 |
| 5,921,997 A * | 7/1999 | Fogelberg et al. | ........... | 606/158 |
| 5,938,667 A * | 8/1999 | Peyser et al. | ................ | 606/142 |
| 5,951,574 A * | 9/1999 | Stefanchik et al. | .......... | 606/143 |
| 5,993,465 A * | 11/1999 | Shipp et al. | ................. | 606/142 |
| 6,053,908 A * | 4/2000 | Crainich et al. | ................ | 606/1 |
| 6,423,079 B1 * | 7/2002 | Blake, III | .................... | 606/143 |
| 6,849,079 B1 * | 2/2005 | Blake, III et al. | ........... | 606/143 |
| 6,869,435 B2 * | 3/2005 | Blake, III | .................... | 606/143 |

* cited by examiner

*Primary Examiner*—Darwin P Erezo
(74) *Attorney, Agent, or Firm*—Baker & Hostetler LLP

(57) ABSTRACT

An apparatus for applying surgical clips includes a jaw assembly and a jaw opening member. The jaw assembly includes first and second opposing pivotable jaw members that define a variable-width jaw aperture therebetween for receiving a clip. The jaw opening member is movable into engagement with the first and second jaw members for increasing the width of the jaw aperture, thereby improving the release of a clip from the jaw assembly.

29 Claims, 38 Drawing Sheets

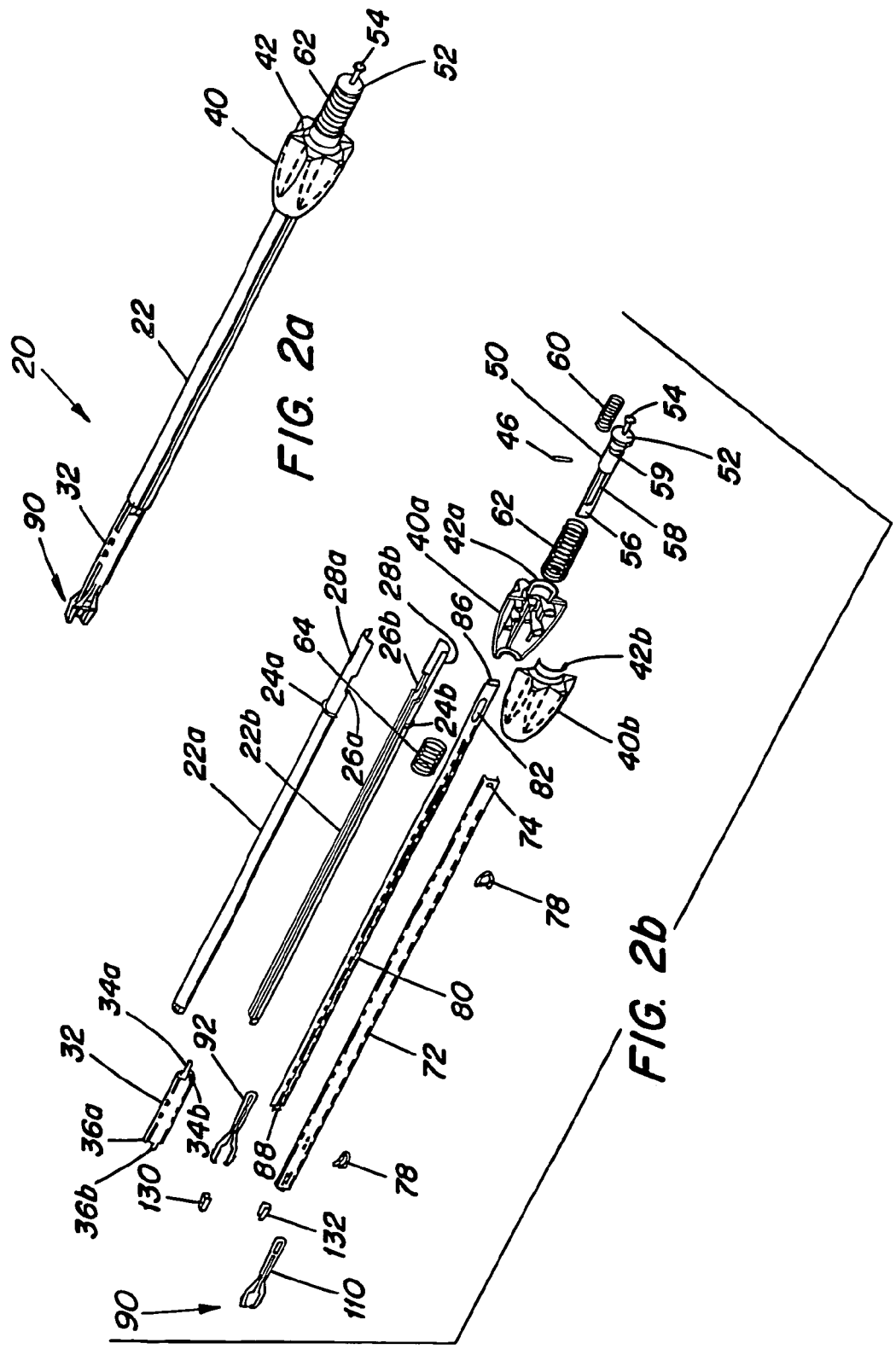

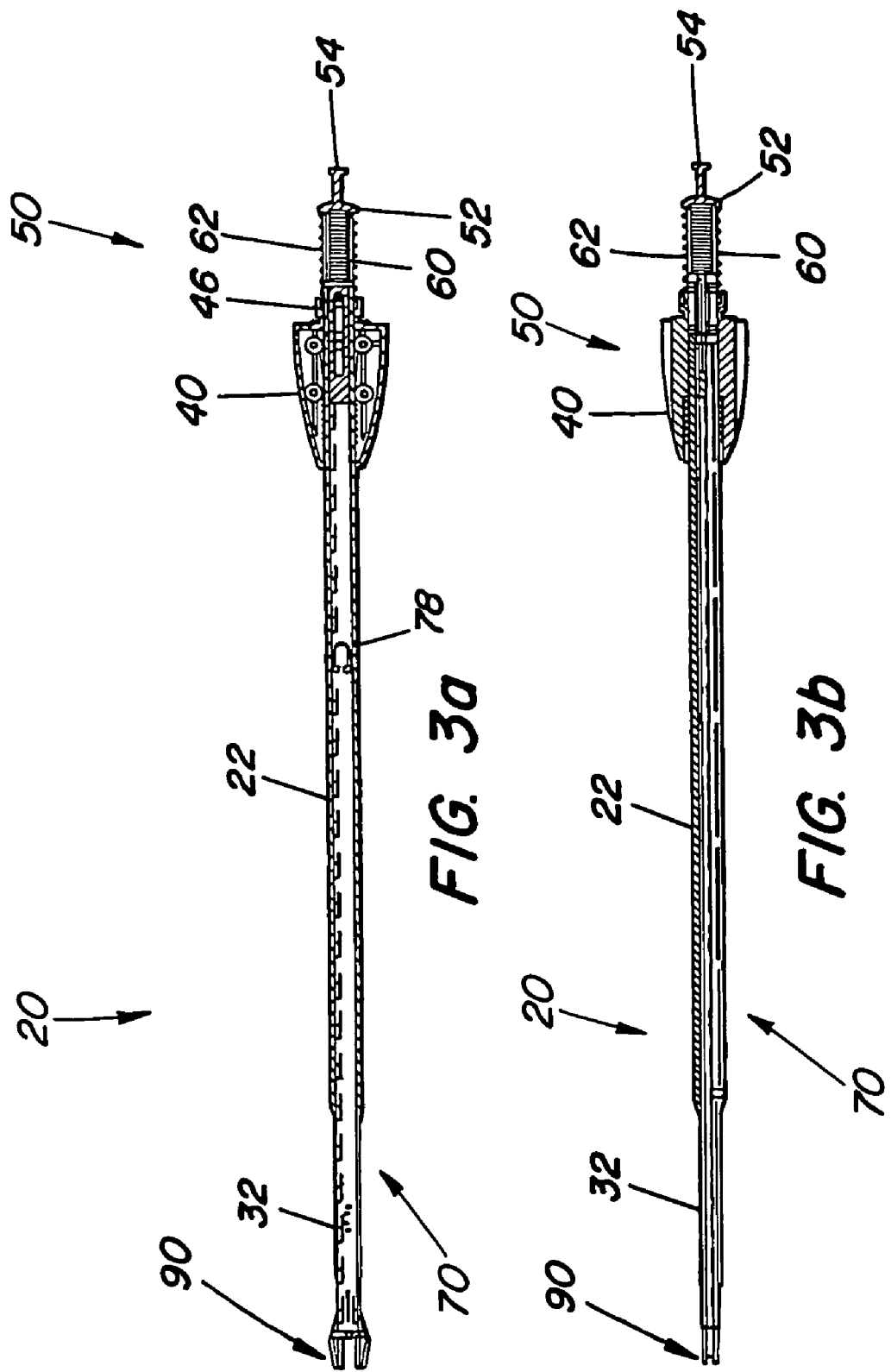

ENDOSCOPIC CLIP APPLYING APPARATUS WITH IMPROVED APERTURE FOR CLIP RELEASE AND RELATED METHOD

TECHNICAL FIELD

The subject matter disclosed herein generally relates to an applier for surgical clips. More particularly, the subject matter disclosed herein relates to an endoscopic ligating clip applier capable of sequentially delivering a number of clips in a clip channel.

BACKGROUND ART

Laparoscopic, endoscopic, and other minimally invasive surgical techniques enable surgeons to perform fairly complicated procedures through relatively small entry points in the body. The term "laparoscopic" refers to surgical procedures performed on the interior of the abdomen, while the term "endoscopic" refers more generally to procedures performed in any portion of the body. Endoscopic surgery involves the use of an endoscope, which is an instrument permitting the visual inspection and magnification of a body cavity. The endoscope is inserted into a body cavity through a cannula extending through a hole in the soft tissue protecting the body cavity. The hole is made with a trocar, which includes a cutting instrument slidably and removably disposed within a trocar cannula. After forming the hole, the cutting instrument can be withdrawn from the trocar cannula. A surgeon can then perform diagnostic and/or therapeutic procedures at the surgical site with the aid of specialized medical instruments adapted to fit through the trocar cannula and additional trocar cannulas providing openings into the desired body cavity.

Some known advantages of minimally invasive surgical techniques include reduced trauma to the patient, reduced likelihood of infection at the surgical site, and lower overall medical costs. Accordingly, minimally invasive surgical techniques are being applied to an increasingly wider array of medical procedures.

Many surgical procedures require body vessels to be ligated during the surgical process. For example, many surgical procedures require cutting blood vessels (e.g., veins or arteries), and these blood vessels may require ligation to reduce bleeding. In some instances a surgeon may wish to ligate the vessel temporarily to reduce blood flow to the surgical site during the surgical procedure. In other instances a surgeon may wish to permanently ligate a vessel.

Vessel ligation may be performed by closing the vessel with a ligating clip, or by suturing the vessel with surgical thread. Performing vessel ligation using surgical thread requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic surgical procedures has grown dramatically.

Ligating clips may be classified according to their geometric configuration as either symmetric clips or asymmetric clips, and according to the material from which they are manufactured. Symmetric clips are generally "U" or "V" shaped metallic clips that are substantially symmetrical about a central, longitudinal axis extending between the legs of the clip. By contrast, asymmetric clips lack an axis of symmetry. For example, U.S. Pat. No. 4,834,096 to Oh et al. describes a polymeric, asymmetric surgical clip in which a first leg member includes a lip that mates with the second leg member to lock the clip in place. Asymmetric clips have certain advantages over symmetric clips. For example, because asymmetric clips are formed from polymeric materials, the mouths of asymmetric clips can be opened wider than the mouths of symmetric clips. This allows a surgeon to position the clip about the desired vessel with greater accuracy. In addition, a clip of the type described in U.S. Pat. No. 4,834,096 can be repositioned before locking the clip on the vessel, a process referred to as "approximating" the clip, or to be removed from the vessel.

Ligating clips are applied using mechanical devices commonly referred to as surgical clip appliers, ligating clip appliers, or hemostatic clip appliers. Surgical clip appliers adapted for endoscopic surgical techniques include a shaft adapted to be inserted through an endoscopic cannula to access a surgical site in a body cavity and a jaw assembly disposed at the distal end of the shaft for retaining a surgical clip. In use, the clip is positioned over the desired vessel and the jaw is actuated, typically using a mechanism disposed in the handle of the device, to close the clip about the vessel.

Multiple clip applier systems have been developed that enable surgeons to deliver multiple symmetric surgical clips to an endoscopic surgical site. In general, these systems provide a surgical clip channel within the shaft of the device and a mechanism for delivering the surgical clips through the shaft to the jaw assembly. For example, U.S. Pat. Nos. 5,100,420 and 5,645,551 to Green et al. describe a device for delivering and applying multiple surgical slips to an endoscopic surgical site. Similarly, U.S. Pat. No. Re 35,525 to Stefanchik et al. aims to provide an endoscopic multiple ligating clip applier with a venting system. U.S. Pat. No. 5,700,271 to Whitfield et al., European Published Patent Application No. 0 409 569 A1, and European Patent No. 0 596 429 B1 propose other clip applier designs.

As endoscopic techniques have been developed, certain inadequacies in the available surgical equipment have become apparent. For example, the jaws of the applier, which are typically used to close a clip around a vessel, may exert unequal pressure on the clip, resulting in a "scissoring" effect and damage to the vessel. In other instances, the clip may not be properly oriented when it is placed within the jaws or may slip out of alignment during application. This may result in the loss or misapplication of the clip. In still other instances, the applier may jam or may simply fail to deploy a clip.

Furthermore, existing multiple clip applier systems have been designed for symmetric clips and are not well suited to satisfy design issues unique to asymmetric clips. For example, symmetric clips can be retained in clip jaws by holding opposing surfaces of the clip's legs in opposing channels. By contrast, asymmetric clips cannot easily be retained in opposing channels because the clip's legs deform when the clip is closed. In addition, when symmetric clips are closed on a vessel, the opposing legs of the clip apply substantially even pressure to the opposing sides of the vessel. By contrast, the opposing legs of an asymmetric clip may apply varying pressure to opposing sides of a vessel when the asymmetric clip is closed. Moreover, locking asymmetric clips of the type described in U.S. Pat. No. 4,834,096 function best when force is applied at or near the distal ends of the clip legs. Still further, asymmetric clips of the type described in U.S. Pat. No. 4,834,096 may need to be placed under compression to be retained in the clip channel. Thus, conventional clip advancing mechanisms designed for symmetric clips may not reliably advance asymmetric clips. In addition, conventional clip advancing mechanisms designed for symmetric clips may not provide the ability to approximate a clip.

Therefore, conventional clip appliers designed for symmetric, metal clips suffer from certain deficiencies and are not adapted to deliver asymmetric, polymer based clips. Accordingly, there is a need to provide an endoscopic clip applier that can reliably deliver a sequence of clips and in a manner which minimizes the risk of damage to the vessel. Additionally, there is a need for an endoscopic clip applier adapted to deliver asymmetric, polymeric ligating clips.

The foregoing problems have been addressed in whole or in part by an endoscopic clip applier adapted for delivering asymmetric, polymeric clips disclosed in copending, commonly assigned U.S. patent application Ser. No. 09/905,679, published as U.S. patent application Publication No. US 2003/0014060 A1, the content of which is incorporated herein in its entirety. In the use of such clip appliers, it has been found that difficulties may sometimes arise when attempting to release an applied clip from the jaws of the clip applier. Specifically, in some instances, clips may tend to become caught or hung up in the jaws in a manner that impedes their easy release therefrom. The subject matter disclosed herein is provided to address this issue.

SUMMARY

According to one embodiment, an apparatus for applying surgical clips comprises a jaw assembly and a jaw opening member. The jaw assembly comprises first and second opposing jaw members defining a jaw aperture therebetween for receiving a clip. The first and second jaw members are pivotable for varying a width of the jaw aperture. The jaw opening member comprises a distal portion generally adjacent to the first and second jaw members. The distal portion is movable into engagement with the first and second jaw members for increasing the width of the jaw aperture.

According to another embodiment, an apparatus for applying surgical clips comprises an elongate assembly, a jaw assembly, and a jaw opening member. The jaw assembly comprises first and second opposing jaw members. The first and second jaw members are pivotably coupled to the elongate assembly, and define a variable-width jaw aperture therebetween for receiving a clip. The jaw opening member is disposed within the elongate assembly and comprises first and second flexible arms that are movable into engagement with the respective first and second jaw members.

According to yet another embodiment, an apparatus for applying surgical clips comprises a jaw assembly, an elongate member, and a jaw opening member. The jaw assembly comprises first and second opposing jaw members defining a jaw aperture therebetween for receiving a clip. The first and second jaw members are pivotable about respective first and second pivot points, and comprise respective first and second outer surfaces. The elongate member is movable into contact with the first and second outer surfaces for pivotably decreasing a width of the jaw aperture. The jaw opening member comprises first and second arms respectively engagable with the first and second outer surfaces for pivotably increasing the width of the jaw aperture.

According to still another embodiment, an apparatus for applying surgical clips comprises a jaw assembly, a feeding device, and a jaw opening member. The jaw assembly comprises first and second opposing jaw members defining a jaw aperture therebetween for receiving a clip. The first and second jaw members are pivotable for varying a width of the jaw aperture. The feeding device is axially movable toward the jaw aperture for feeding a clip therein. The jaw opening member is engagable with the feeding device for movement therewith, and is movable into engagement with the first and second jaw members for increasing the width of the jaw aperture.

In addition, a method is disclosed herein for improving the release of a clip from a clip applying apparatus. A jaw assembly of the clip applying apparatus is opened to increase a width of a jaw aperture defined between first and second opposing jaw members of the jaw assembly. A biasing force is imparted to the first and second jaw members to further increase the width of the jaw aperture, whereby the further increased width facilitates releasing the clip disposed in the jaw aperture from the clip applying apparatus.

It is therefore an object of the subject matter disclosed herein to provide an endoscopic clip applier with improved aperture for clip release and a method for increasing the jaw aperture so as to improve clip release.

An object having been stated hereinabove, and which is addressed in whole or in part by the subject matter disclosed herein, other objects will become evident as the description proceeds when taken in connection with the accompanying drawings as best described hereinbelow.

BRIEF DESCRIPTION OF THE DRAWINGS

FIG. 2A is a perspective view of the shaft assembly of a clip applier in accordance with the subject matter disclosed herein;

FIG. 2B is an assembly view of the shaft assembly depicted in FIG. 2A;

FIG. 3A is a cross-sectional view of a shaft assembly of a clip applier in accordance with the subject matter disclosed herein, taken in a plane parallel to jaw members of the shaft assembly;

FIG. 3B is a cross-sectional view, taken in a plane perpendicular to the jaw members, of the shaft assembly depicted in FIG. 3A;

DETAILED DESCRIPTION OF THE INVENTION

Figure 1:
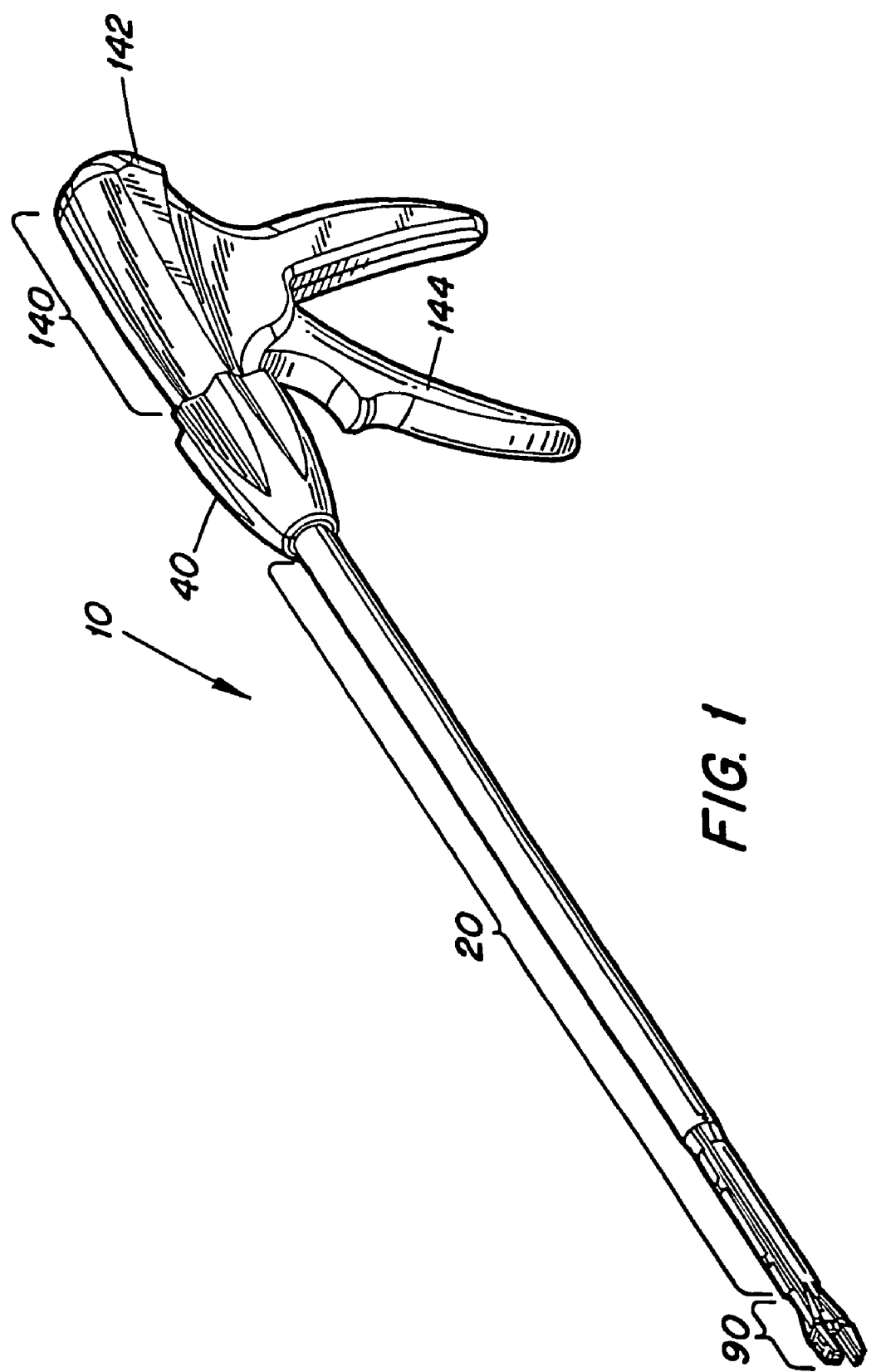
FIG. 1 is a perspective view of a clip applier constructed in accordance with the subject matter disclosed herein.

Referring to FIG. 1, an exemplary embodiment of an endoscopic clip applier 10 in accordance with the subject matter disclosed herein includes an elongate or shaft assembly generally designated 20, a jaw assembly generally designated 90 disposed at a distal end thereof, and a handle assembly generally designated 140 disposed at a proximal end thereof. Handle assembly 140 includes a stationary grip 142 and a movable trigger 144 for actuating clip applier 10. In use, jaw assembly 90 may be positioned inside a body cavity, for example by passing shaft assembly 20 through an endoscopic cannula, to apply a ligating clip to a body vessel.

Figure 2C:
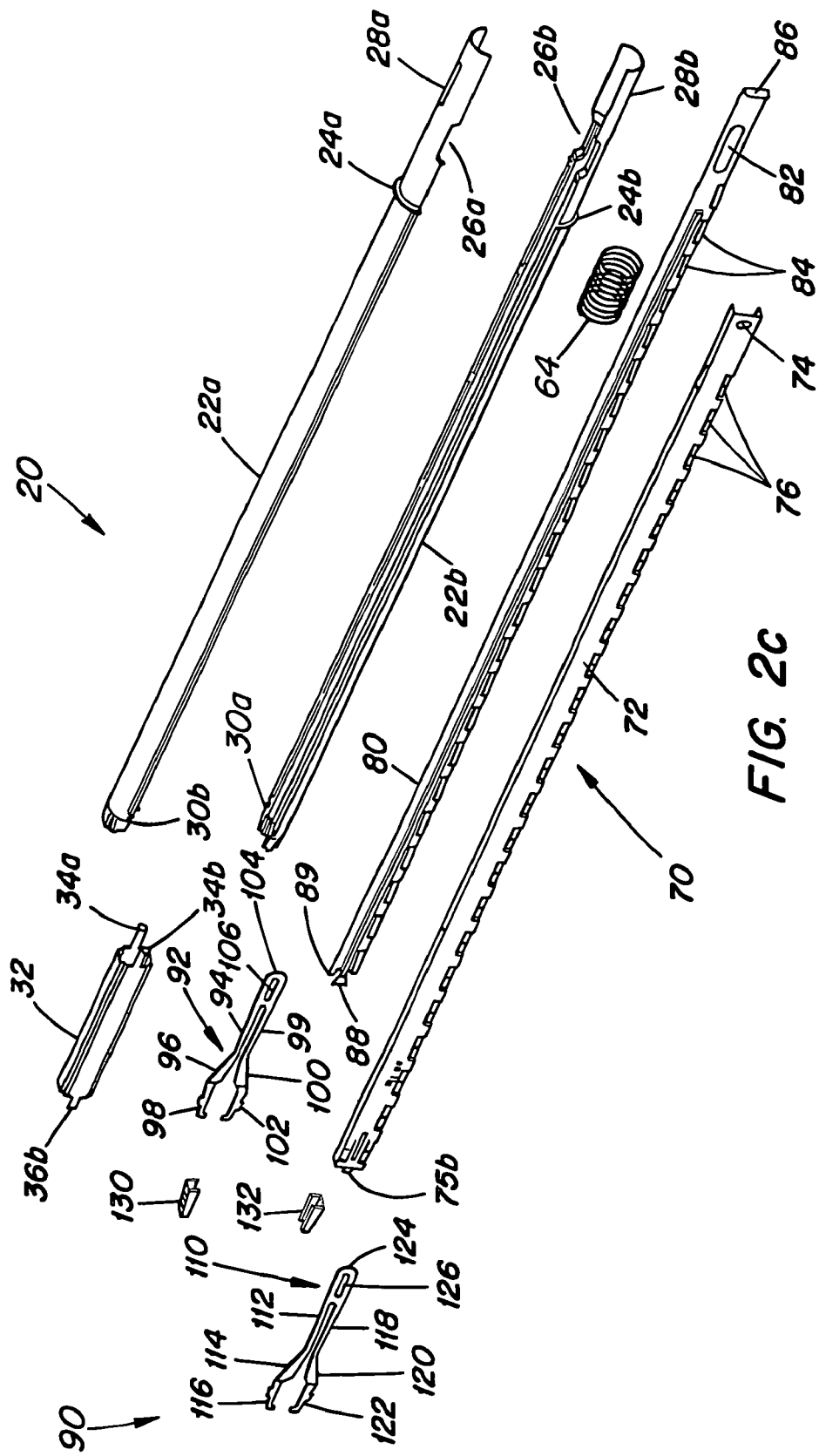
FIG. 2C is an enlarged assembly view of portions of the shaft assembly depicted in FIG. 2B.

FIG. 2A is a perspective view and FIGS. 2B and 2C are exploded assembly views of an exemplary embodiment of shaft assembly 20 and jaw assembly 90. Shaft assembly 20 includes an elongate member such as a cylindrical outer shaft member 22, which may be formed from two semi-cylindrical outer shaft members 22A and 22B, respectively. It will be appreciated that outer shaft member 22 may be formed from a single tubular member, or may be of a rectangular or polygonal cross-section. Outer shaft member 22 includes a proximal flange, indicated by proximal flange half sections 24A, 24B extending from the cylindrical surface of shaft members 22A and 22B, respectively. Outer shaft member 22 further includes pin slots 28A, 28B formed in the cylindrical surface. In addition, the cylindrical surfaces of outer shaft members 22A, 22B include opposing channels 26A, 26B that define opposing slots when shaft member 22 is assembled. Outer shaft 22 may be formed from a suitably rigid material, e.g., a suitable polymer or metal.

Figure 18:
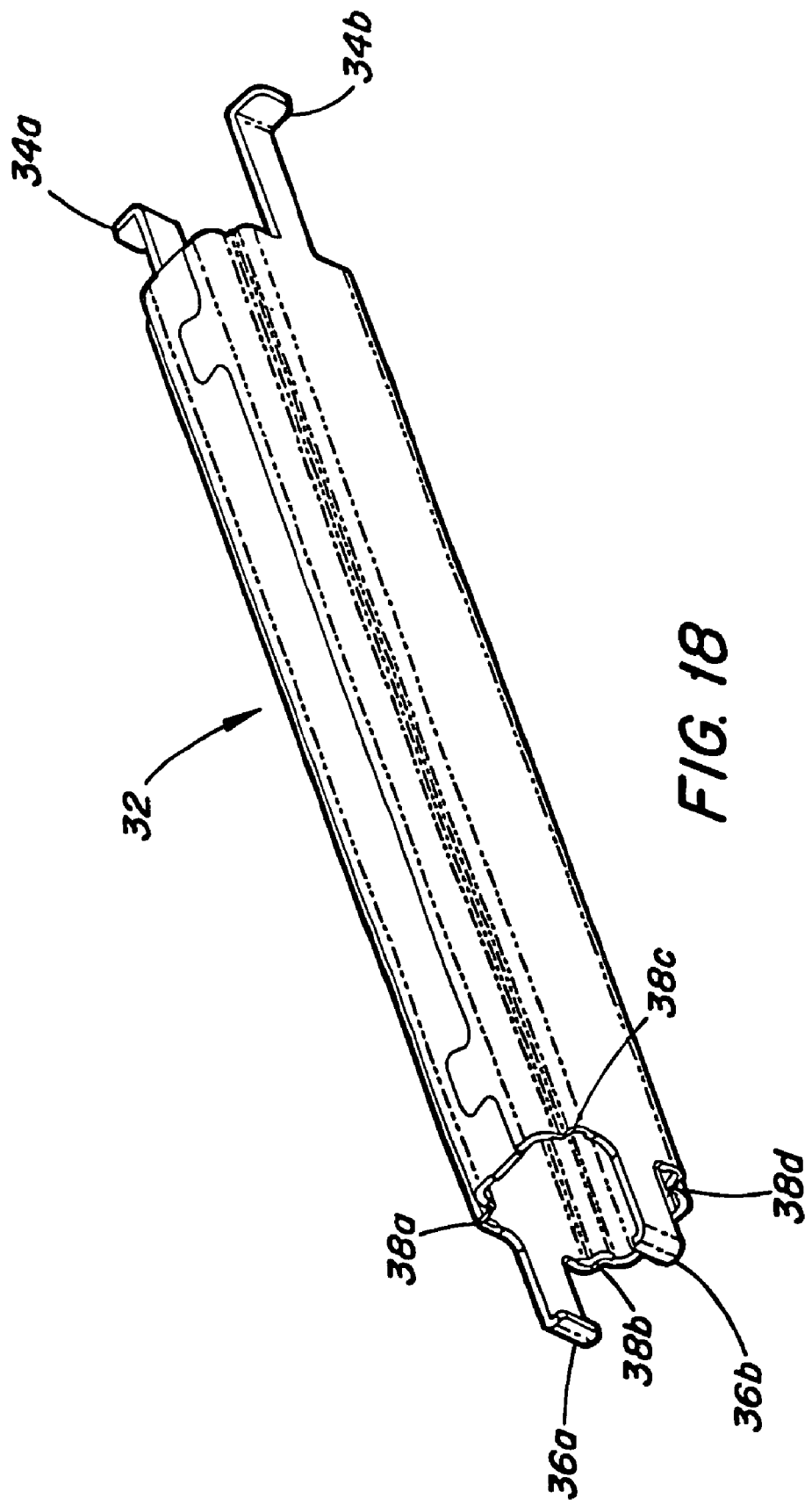
FIG. 18 is a perspective view of a collar in accordance with an embodiment of the subject matter disclosed herein.

With further reference to FIGS. 2A-2C, at the distal end, shaft 22 may taper from a cylindrical cross-section to a substantially rectangular cross-section. As best shown in FIG. 2C, the distal end section of shaft assembly 20 can include a collar 32, which can be a separate component from outer shaft 22. Collar 32 has keys 34A, 34B that interlock with key slots 30A, 30B formed in one or both of outer shaft members 22A, 22B for connecting collar 32 to outer shaft member 22. As best shown in FIG. 18, collar 32 preferably is substantially rectangular in cross-section and includes four cam surfaces 38A, 38B, 38C, 38D and opposing keys 36A, 36B at its distal end. As also shown in FIG. 18, collar 32 can also be constructed from two pieces of halves. Collar 32 may be formed from suitably rigid material, e.g., a suitable polymer or metal. In other embodiments, outer shaft member 22 continuously transitions into collar 32 as a unitary structure. For instance, in the case of a two-piece unitary structure, outer shaft members 22A and 22B can include distal sections that, when assembled together, form collar 32. Hence, collar 32 in at least some embodiments can be considered a collar portion or distal portion of outer shaft member 22, as illustrated for example in the embodiment shown in FIGS. 26A-30.

Referring to FIG. 2C, a clip feed assembly, generally designated 70, is disposed within outer shaft 22 and collar 32. Clip feed assembly 70 includes a channel 72 for housing clips 78 (FIG. 2B), and a feeder bar 80 that is movable along the longitudinal axis of shaft 22 for moving clips 78 disposed in channel 72 toward the distal end of clip applier 10. Channel 72 includes a pin hole 74 near the proximal end and a plurality of tabs 76 near its base. Channel 72 may be formed from suitably rigid material, e.g., a suitable polymer or metal.

Feeder bar 80 includes a pin slot 82 and a plurality of tabs 84 which act as clip advancing elements to move clips 78 in channel 72 toward the distal end of clip applier 10. Each tab 84 may be formed by stamping or cutting a portion of the body of feeder bar 80. Tab 84 remains attached to the body of feeder bar 80 at the proximal end of tab 84. Each tab 84 may be bent or otherwise directed toward the interior of the clip channel 72. Tabs 84 may have a substantially uniform length, which may be determined by the length and geometry of the endoscopic clip, and by the rigidity of the material from which feeder bar 80 is manufactured. Tabs 84 may be located along either the top or bottom (or both) edges of the side of clip channel 72. Feeder bar 80 may be formed from suitably rigid material, e.g., a suitable polymer or metal.

As shown in FIG. 2B, shaft assembly 20 further includes a linking member or yoke, generally designated 50, a portion of which is disposed within handle assembly 140 (FIG. 1), for translating longitudinal motion to feeder bar 80 and outer shaft 22. Feeder bar 80 includes a tab 86 that rests adjacent an interior distal edge 57 of yoke 50 (see also FIG. 15C). A portion of the yoke body 56 extends along a portion of the length of feeder bar 80 and has a slot 58 that aligns with pin slot 82 when yoke 50 is connected to feeder bar 80. Yoke 50 further includes a flange 52 and pin 54 on its proximal end. Yoke 50 may be formed from suitably rigid material, e.g., a suitable polymer or metal. A feeder spring 60 is positioned within body 56 of yoke 50 for biasing feeder bar 80 toward the distal end of yoke 50. A tube spring 62 is positioned between flange 52 and a flange 42 (e.g., flange halves 42A and 42B) on knob 40 for biasing yoke 50 toward the proximal end of shaft assembly 20. A knob spring 64 is disposed within knob 40 and biases outer shaft 22 in a proximal direction.

Referring to FIG. 2C, jaw assembly 90 is connected to the distal end of clip channel 72. Jaw assembly 90 includes a first jaw member 92 having a first leg 94 and a second leg 99 connected by a bridge member 104. First leg 94 includes a first cam surface 96 and a first jaw arm 98, a second leg 99 includes a second cam surface 100 and a second jaw arm 102. Bridge member 104 includes a slot 106 for receiving a conventional fastener (e.g., rivets, pins, screws, tabs, etc.) to connect first jaw member 92 to clip channel 72. Jaw assembly 90 further includes a second jaw member 110 having a third leg 112 and a fourth leg 118 connected by a bridge member 124. Third leg 112 includes a third cam surface 114 and a third jaw arm 116, and fourth leg 118 includes a fourth cam surface 120 and a fourth jaw arm 122. Bridge member 124 includes a slot 126 for receiving a conventional fastener (e.g., rivets, pins, screws, tabs, etc.) to connect second jaw member 110 to clip channel 72. Jaw assembly 90 further includes a first guide 130 adapted to clip over first jaw arm 98 and third jaw arm 116 and a second guide 132 adapted to clip over second jaw arm 102 and fourth jaw arm 122. Jaw assembly 90 may be formed from suitably rigid material, e.g., a suitable polymer or metal.

FIGS. 3A and 3B are cross-sectional views of an assembled shaft assembly 20 of a clip applier 10 in accordance with the subject matter disclosed herein. When assembled, jaw assembly 90, clip feed assembly 70, and yoke 50 are connected as described herein and extend through outer shaft 22. Knob 40 is mounted to the exterior of outer shaft 22 and secured using conventional fasteners (e.g., pins, rivets, screws, adhesives, etc.). A pin 46 extending through knob 40 and through pin hole 74 (FIG. 2C) in clip channel 72 retains clip channel 72 in a fixed position with respect to knob 40. For clarity, FIG. 3A illustrates a clip channel 72 having a single clip 78, but it will be appreciated that clip channel 72 may be filled with a plurality (e.g., 2-100) clips. The diameter of outer shaft 22 can generally be determined by the diameter of the cannula through which outer shaft 22 must pass to enter a body cavity. Many existing surgical procedures use a cannula having an inner diameter measuring approximately 10 millimeters. Accordingly, in one embodiment of the invention, outer shaft 22 has an outer diameter slightly less than 10 millimeters. In an alternate embodiment, outer shaft 22 may be dimensioned to fit within a cannula having a diameter of 5 millimeters. It will be appreciated, however, that the diameter of outer shaft 22 is not critical to the invention; any other diameter may be used as desired.

Figure 4:
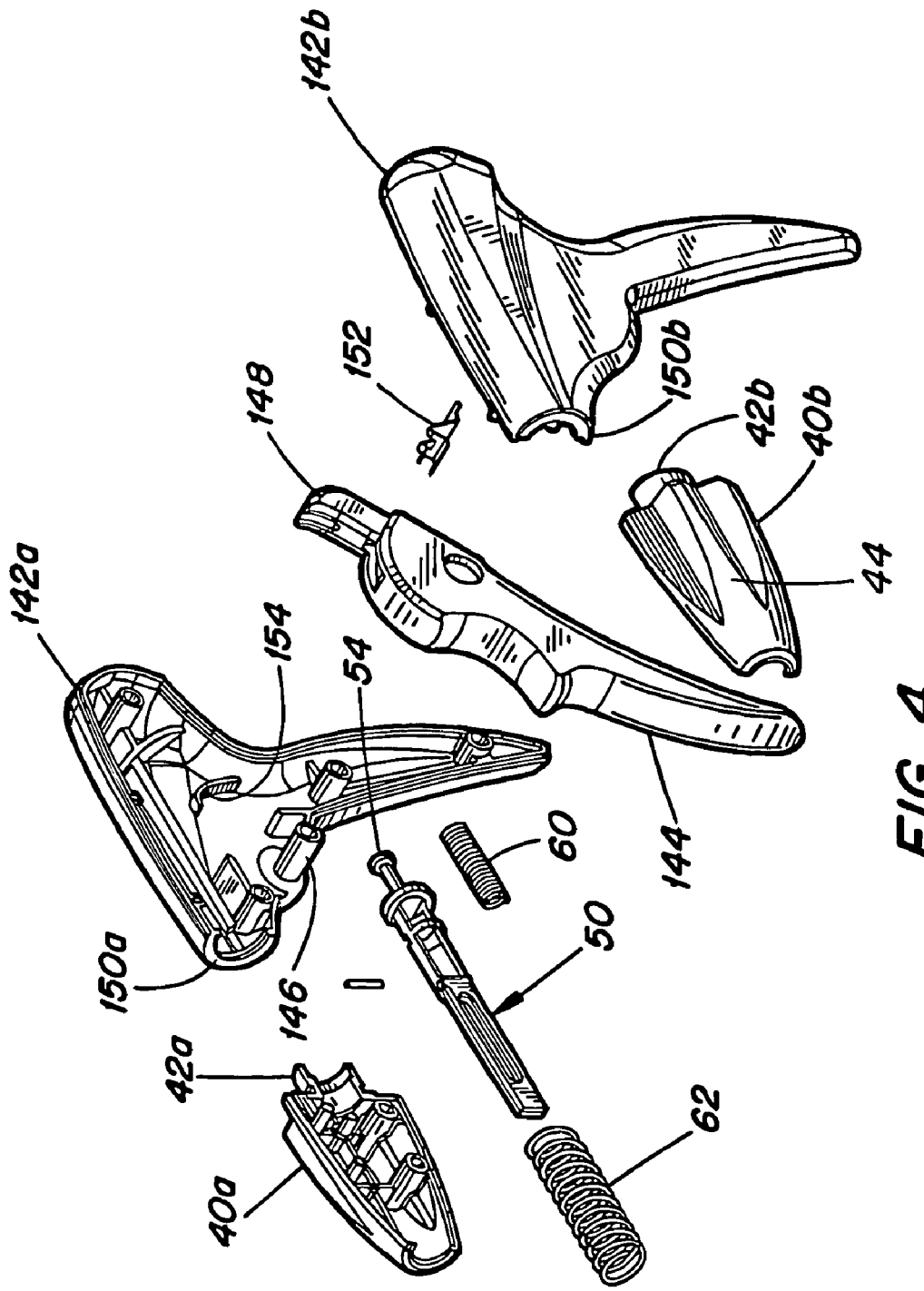
FIG. 4 is an assembly view of a handle assembly in accordance with the subject matter disclosed herein.
Figure 5:
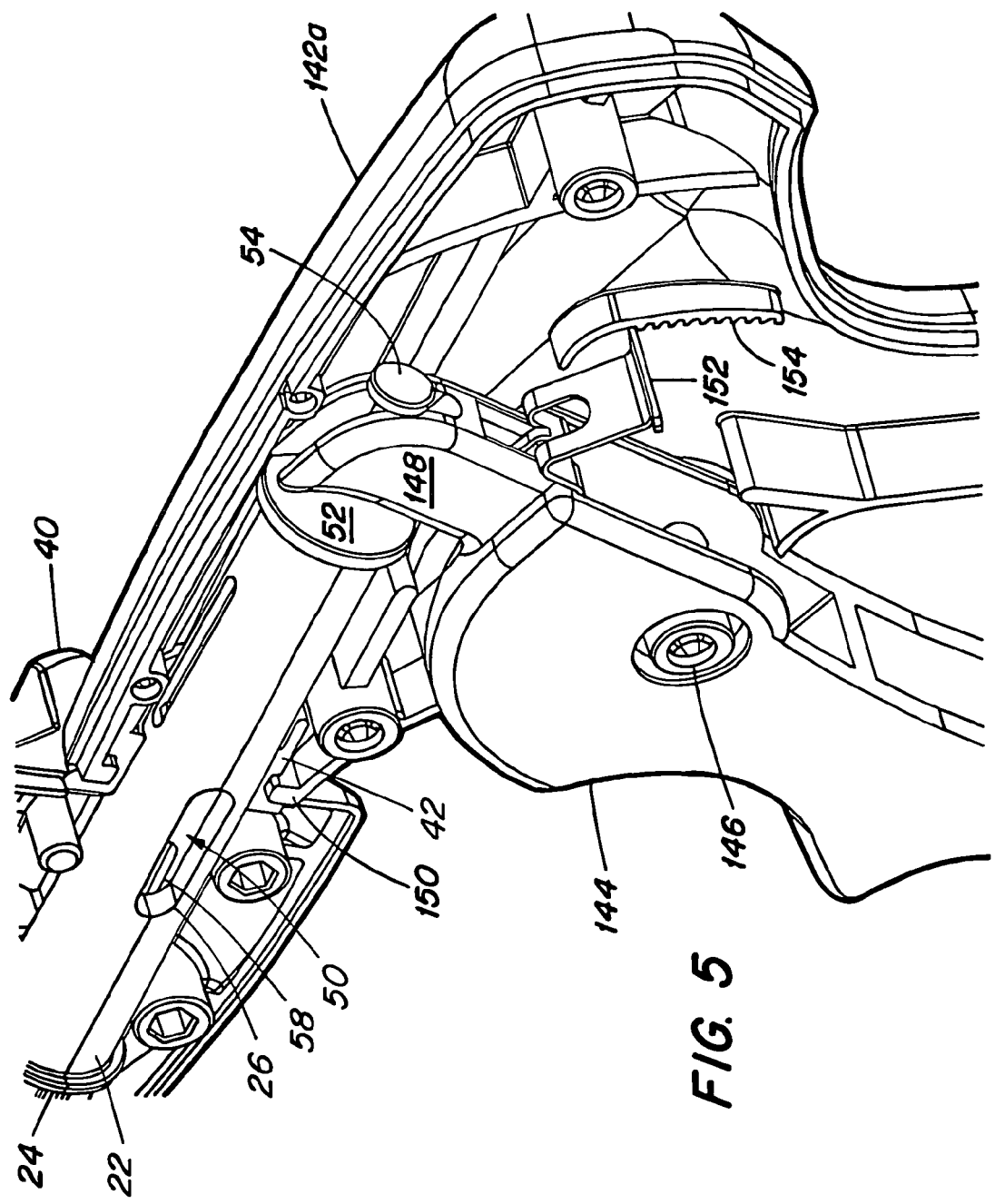
FIG. 5 is a perspective view of the interior of a handle assembly in accordance with the subject matter disclosed herein.

Referring to FIGS. 4 and 5, handle assembly 140 includes a fixed grip 142, which may be manufactured in two substantially symmetrical parts 142A, 142B. A trigger 144 is pivotally mounted to fixed grip 142 about a pivot point 146. As best shown in FIG. 5, trigger 144 includes a grooved claw 148 that impinges on flange 52 to translate the rotary motion of trigger 144 about pivot point 146 to linear motion of yoke 50 relative to fixed grip 142 in the distal direction. Grooved claw 148 also receives pin 54 of yoke 50. This arrangement enables a user to force yoke 50 in a proximal direction if necessary, which provides a safety feature. Fixed grip 142 further includes a rim 150 that secures flange 42 of knob 40, such that knob 40 and clip channel 72 are maintained in a substantially fixed longitudinal position relative to fixed grip 142. The entire shaft assembly 20 is rotatable about its longitudinal axis, and knob 40 includes fins 44 (FIG. 4) that facilitate rotating the shaft assembly 20.

A ratchet key 152 extends from the rear of trigger 144 and contacts ratchet guide 154 to inhibit backward motion of trigger 144 through a portion of the actuation stroke. Preferably, the toothed surface portion of ratchet guide 154 corresponds to the range of motion trigger claw 148 covers while feeder bar 80 is moved forward to advance the clips in clip channel 72 (i.e., the feed stroke). The smooth surface portion of ratchet guide 154 preferably corresponds to the range of motion trigger claw 148 covers during the portion of the actuation stroke that closes jaw assembly 90. When the device is actuated, the transition of ratchet key 152 from the ratchet surface portion to the smooth surface portion provides the user with tactile feedback indicating that the feed stroke is complete and a clip 78 has been fed to jaw assembly 90. In addition, the smooth surface portion permits a user to approximate clip 78.

Basic structural elements of one embodiment of a clip applier 10 have been described with reference to FIGS. 1-5. Alternate embodiments for some components, and the interaction of the structural elements and general operation of the device, will be described with reference to FIGS. 6-30.

Figure 6:
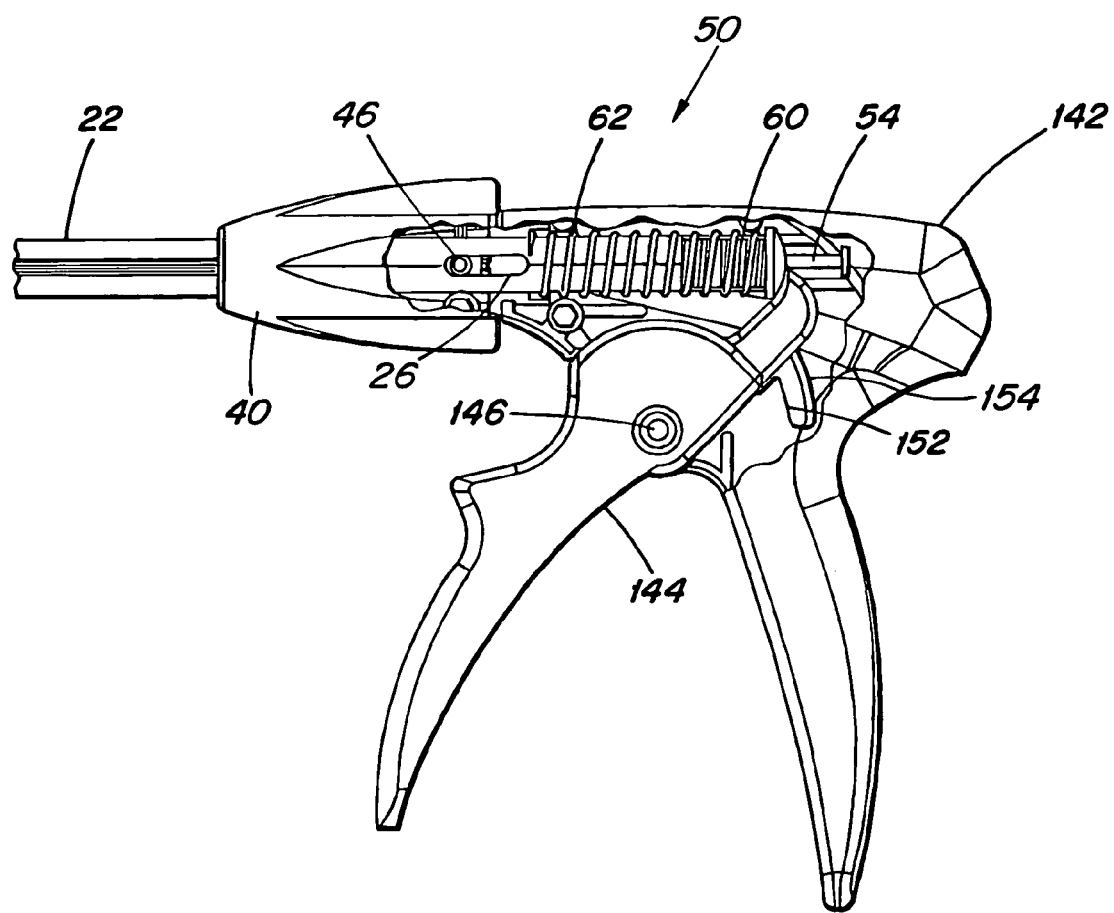
FIG. 6 is a partial cut-away view of a handle assembly in accordance with the subject matter disclosed herein.

FIG. 6 is a partial cut-away, side view of the proximal end of clip applier 10 with the device in an unactuated state. Referring to FIG. 6, yoke 50 is biased to its most proximal position by tube spring 62. In the unactuated state, jaw assembly 90 is partially open, as depicted in FIG. 1. Trigger 144 and yoke 50, in combination, may be considered an actuation assembly for actuating clip feed assembly 70 and jaw assembly 90.

Figure 7:
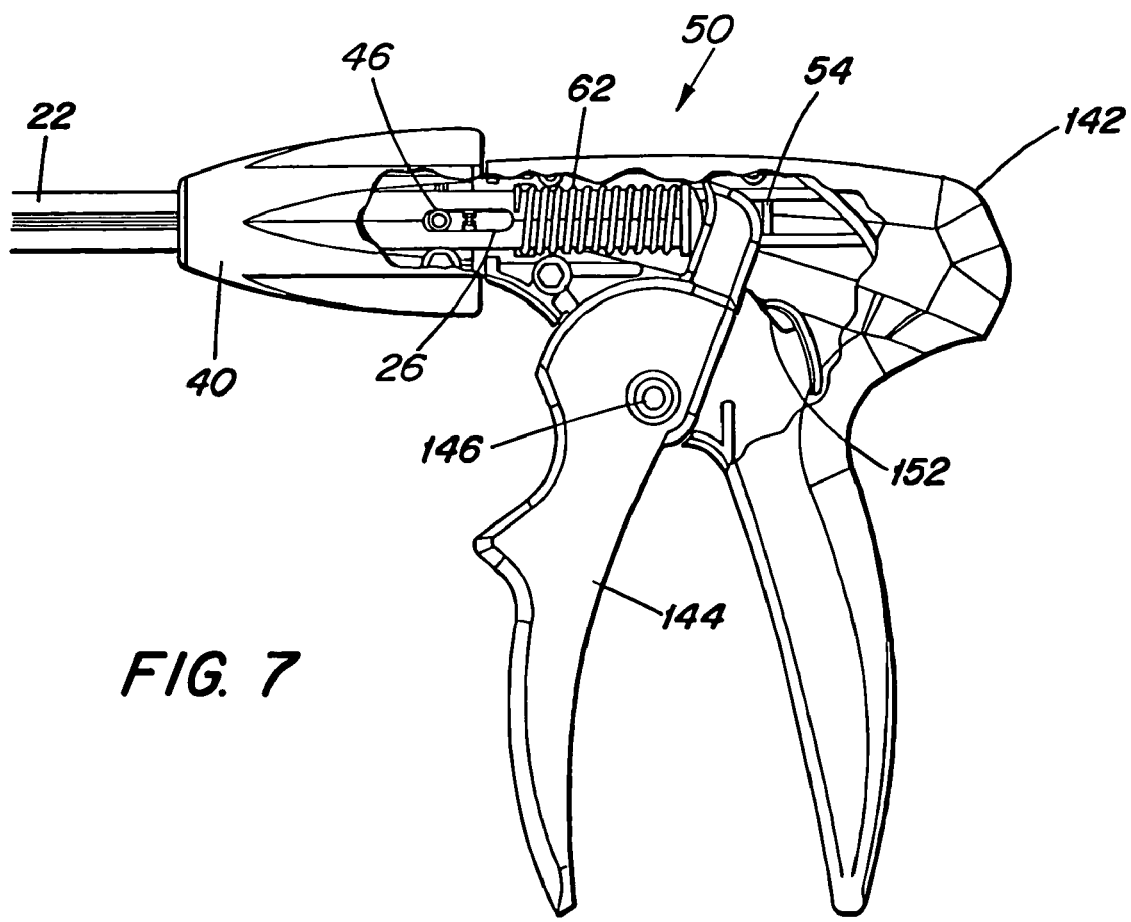
FIG. 7 is a partial cut-away view of a handle assembly in accordance with the subject matter disclosed herein.

FIG. 7 is a side cut-away view of the proximal end of clip applier 10 with the device in a partially actuated state. Forward motion of yoke 50 places tube spring 62 under compression. In one embodiment, the spring coefficient of feeder spring 60 (FIG. 6) is higher than the amount of force required to advance feeder bar 80. Therefore, feeder spring 60 effectively functions as a solid piece of material during the feed stroke.

Figure 8:
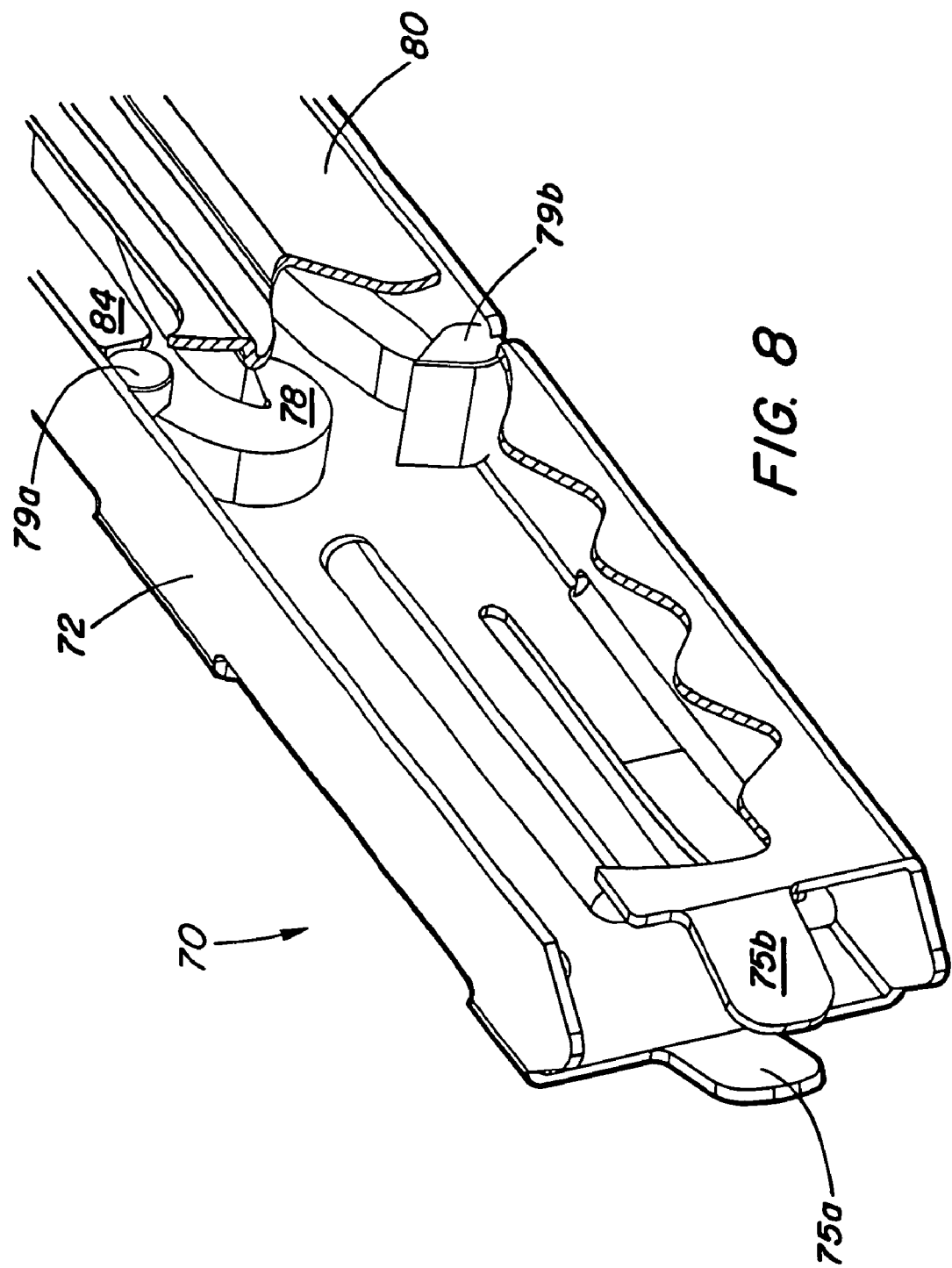
FIGS. 8-10 are sequential, partial cut-away views of a clip channel during a clip advancing process.
Figure 9:
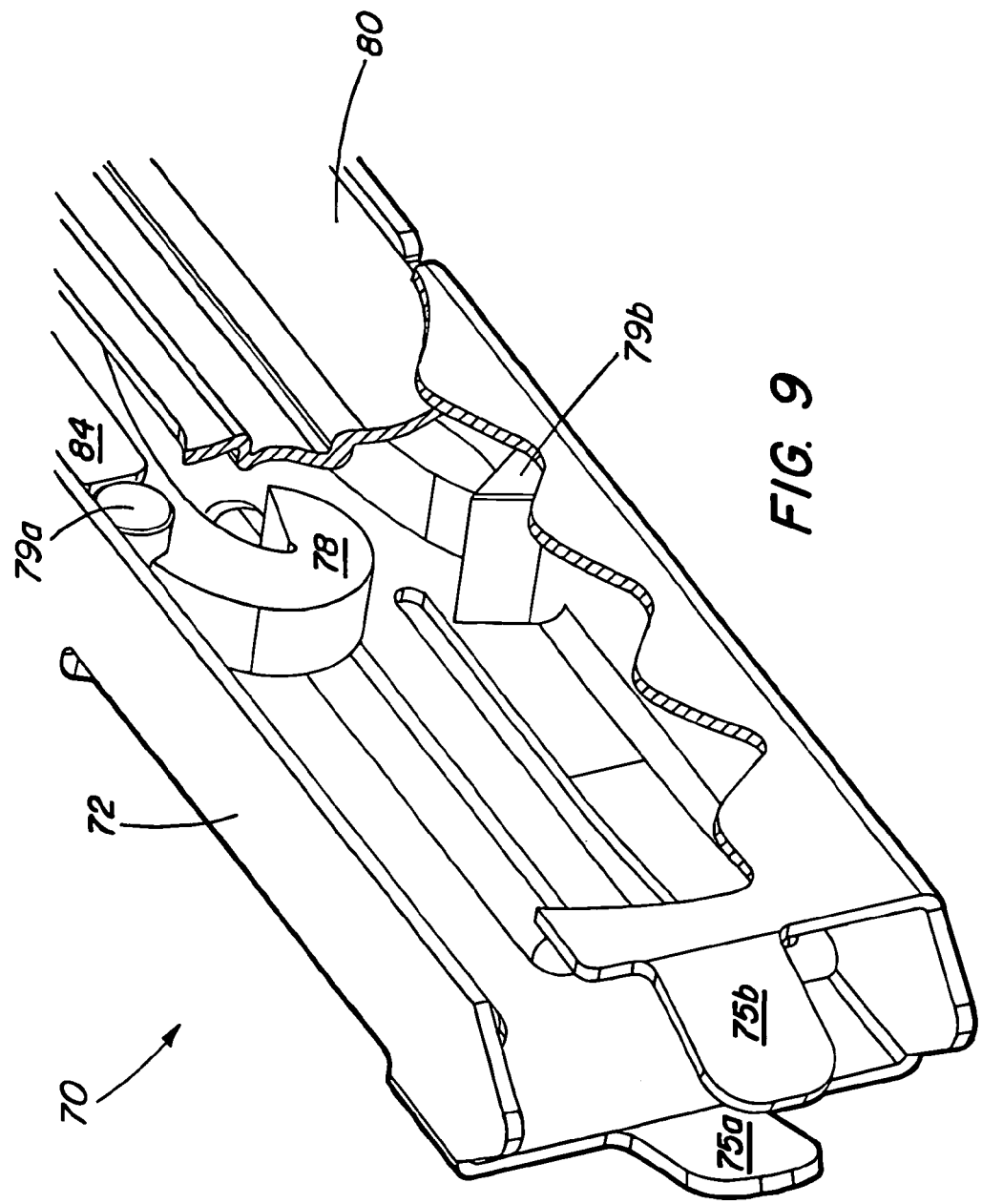
Figure 10:
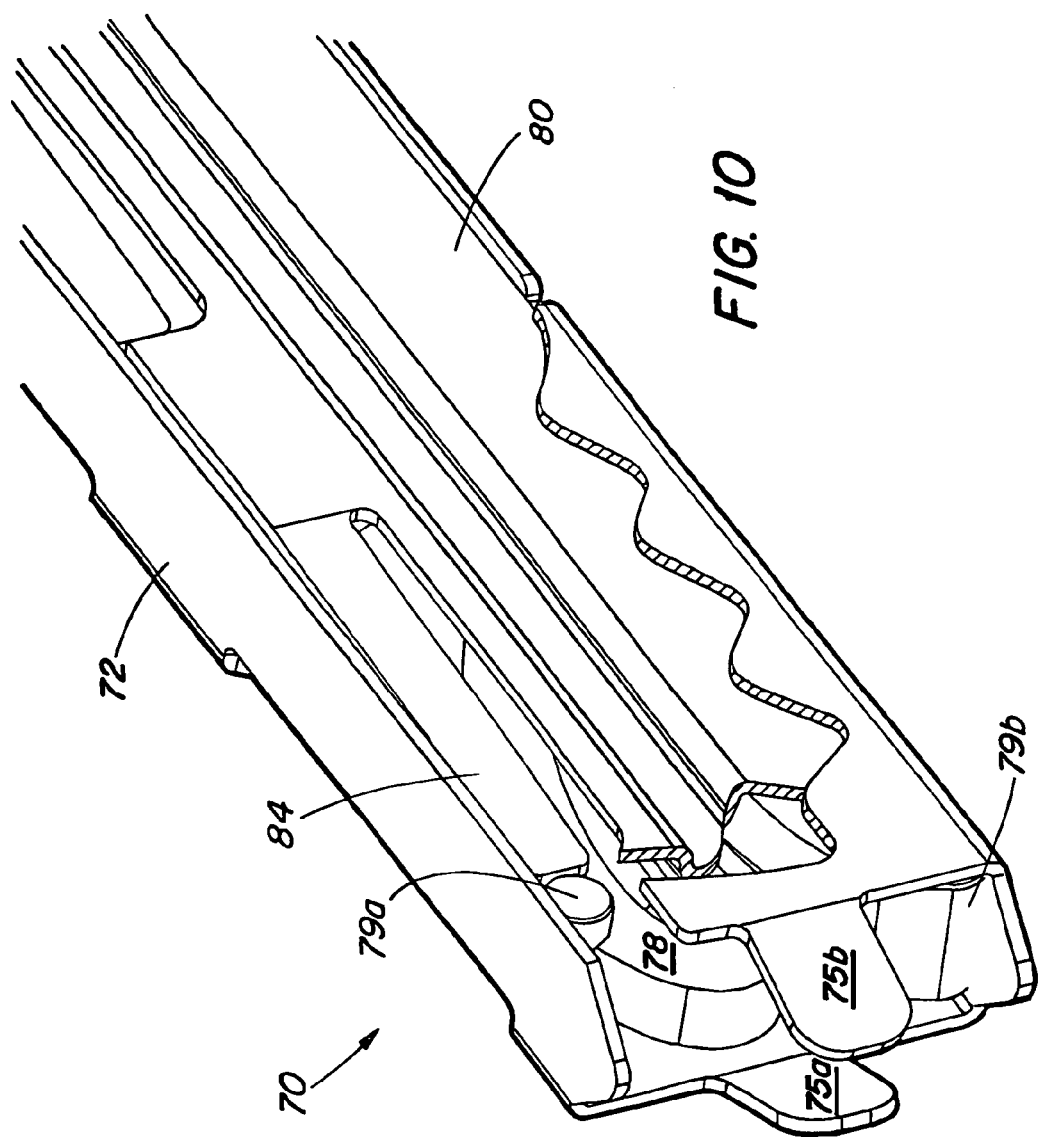

Referring generally to FIGS. 6-8, according to one embodiment, the first portion of the stroke of trigger 144 is a feed stroke that advances yoke 50 and feeder bar 80 relative to the fixed clip channel 72. When feeder bar 80 is advanced, tabs 84 engage clips 78 in clip channel 72 and advance clips 78 toward the distal end of clip applier 10. The most distal clip 78 is fed into jaw assembly 90 (FIG. 1). FIGS. 8-10 are partial cut-away views of clip feeder assembly 70 illustrating the advancement or indexing of clip 78 to the most distal position during the feed stroke. For clarity of illustration, the distal end of feed bar 80 has been cut-away in FIGS. 8-10. FIG. 8 illustrates the beginning of a feed stroke, in which tab 84 of feeder bar 80 is brought into contact with a boss 79A of clip 78 disposed in clip channel 72. In FIG. 9, further actuation of trigger 144 (FIGS. 6 and 7) moves feeder bar 80 in a distal direction, which advances clip 78 toward the distal end of clip channel 72. In FIG. 10, feeder bar 80 has advanced clip 78 to the most distal position in clip channel 72. For clarity, FIGS. 8-10 illustrate the advance of a single clip 78 toward the distal end of clip applier 10, but it will be appreciated that clip channel 72 may include a plurality (e.g., 2-100) of clips 78, each of which is advanced by a tab 84 of feeder bar 80. In one exemplary embodiment, clip channel 72 holds twenty (20) clips 78.

Figure 19:
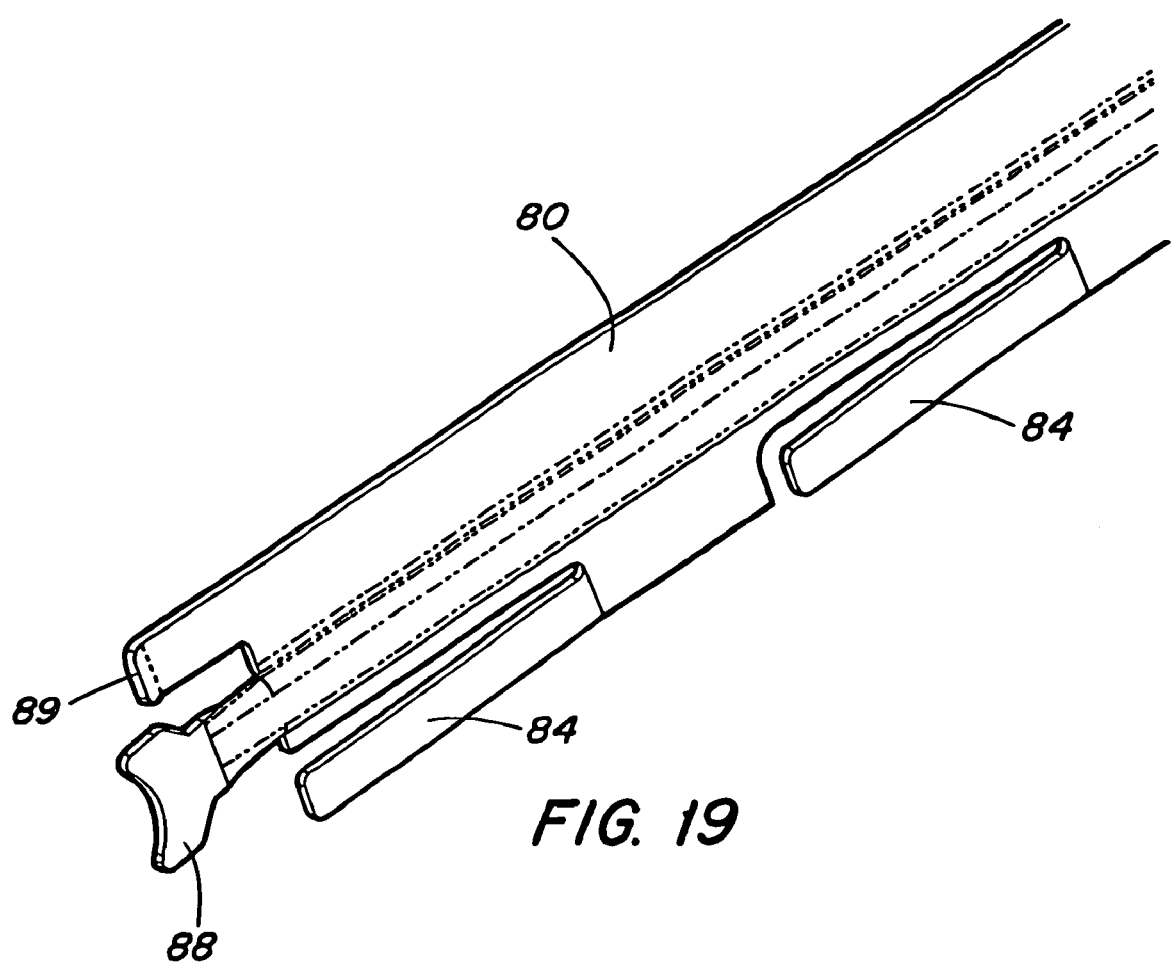
FIG. 19 is a perspective view of the distal end of a feeder bar in accordance with an embodiment of the subject matter disclosed herein.

During the feed stroke, the most distal clip 78 is fed from clip channel 72 to jaw assembly 90. In an exemplary embodiment, the distal end of clip channel 72 and feeder bar 80 include structural features adapted to feed the most distal clip 78 into jaw assembly 90. Referring to FIG. 19, the distal end of feeder bar 80 includes a feeder tab 88 adapted to contact the central rear portion of the most distal clip 78 to push clip 78 into jaw assembly 90. In addition, feeder bar 80 includes a foot member 89 that rotates the rear of the most distal clip 78 during the return stroke so the rear portion of clip 78 is positioned to contact feeder tab 88. Preferably, the interior surfaces of jaw assembly 90 that receive clips 78 are of substantially the same width as clip channel 72 to provide a smooth transition between the clip channel 72 and jaw assembly 90.

Figure 20:
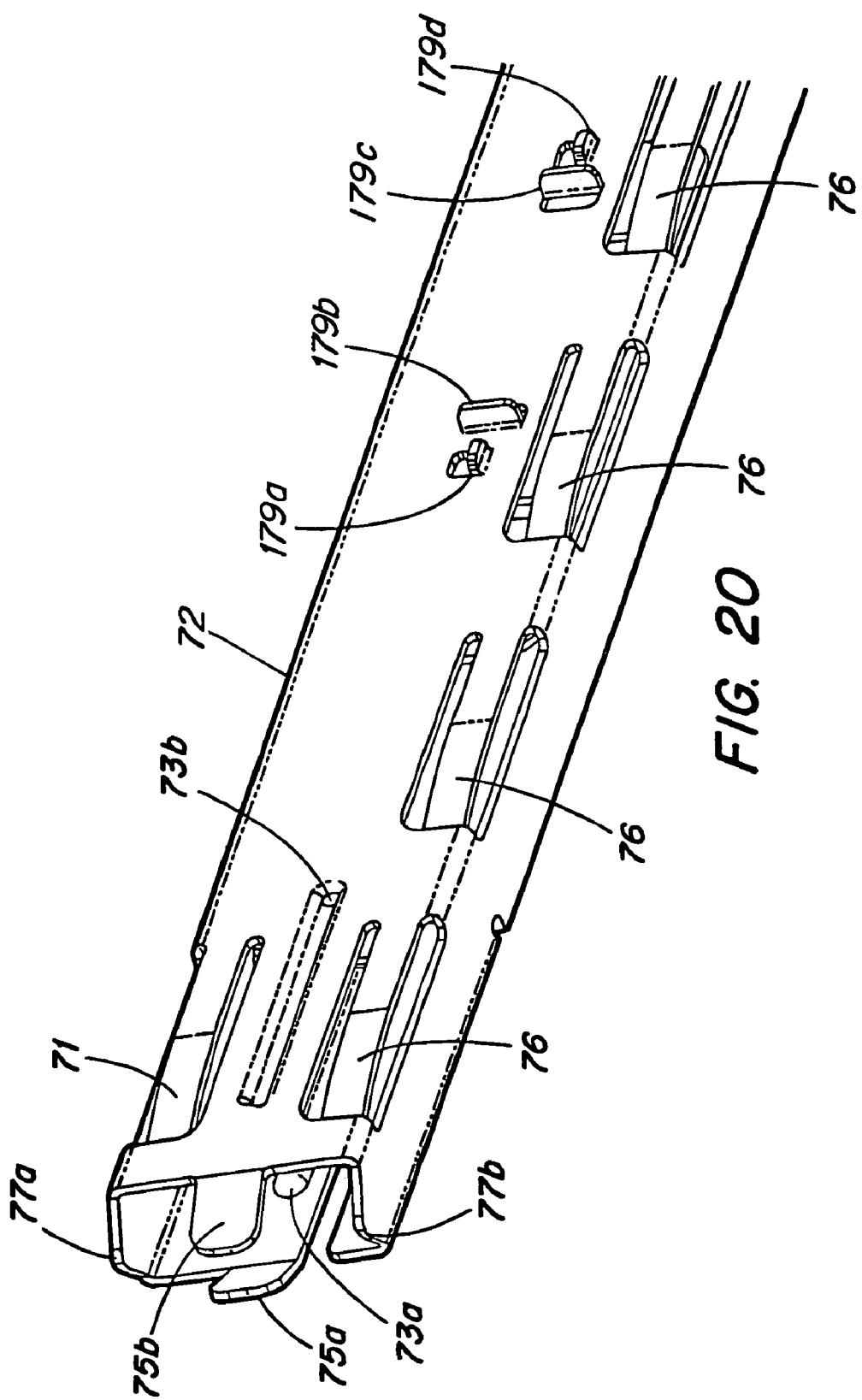
FIG. 20 is a perspective view of the distal end of a clip channel in accordance with an embodiment of the subject matter disclosed herein.

Referring to FIG. 20, the distal end of clip channel 72 includes a tab 71 that catches the boss on the most distal clip 78 when foot member 89 (FIG. 19) of feeder bar 80 rotates clip 78 during the return stroke, thereby limiting the rotation of clip 78. In addition, opposing ribs 73A, 73B facilitate centering the rear of the most distal clip 78 (in the lateral direction) so the rear portion of clip 78 is positioned to contact feeder tab 88 (FIG. 19). The distal end of clip channel 72 further includes upper and lower tabs 77A, 77B to provide a surface that facilitates the transfer of clip 78 into jaw assembly 90. In addition, opposing lateral tabs 75A, 75B serve to guide clip 78 into jaw assembly 90 and to inhibit lateral motion of the rear portion of clip 78 when clip 78 is in jaw assembly 90. FIG. 20 also provides a view of tabs 76 that inhibit clips 78 from sliding in a proximal direction during the return stroke of feeder bar 80, and of tabs 179A-179D for securing a jaw component to clip channel 72.

Figure 12:
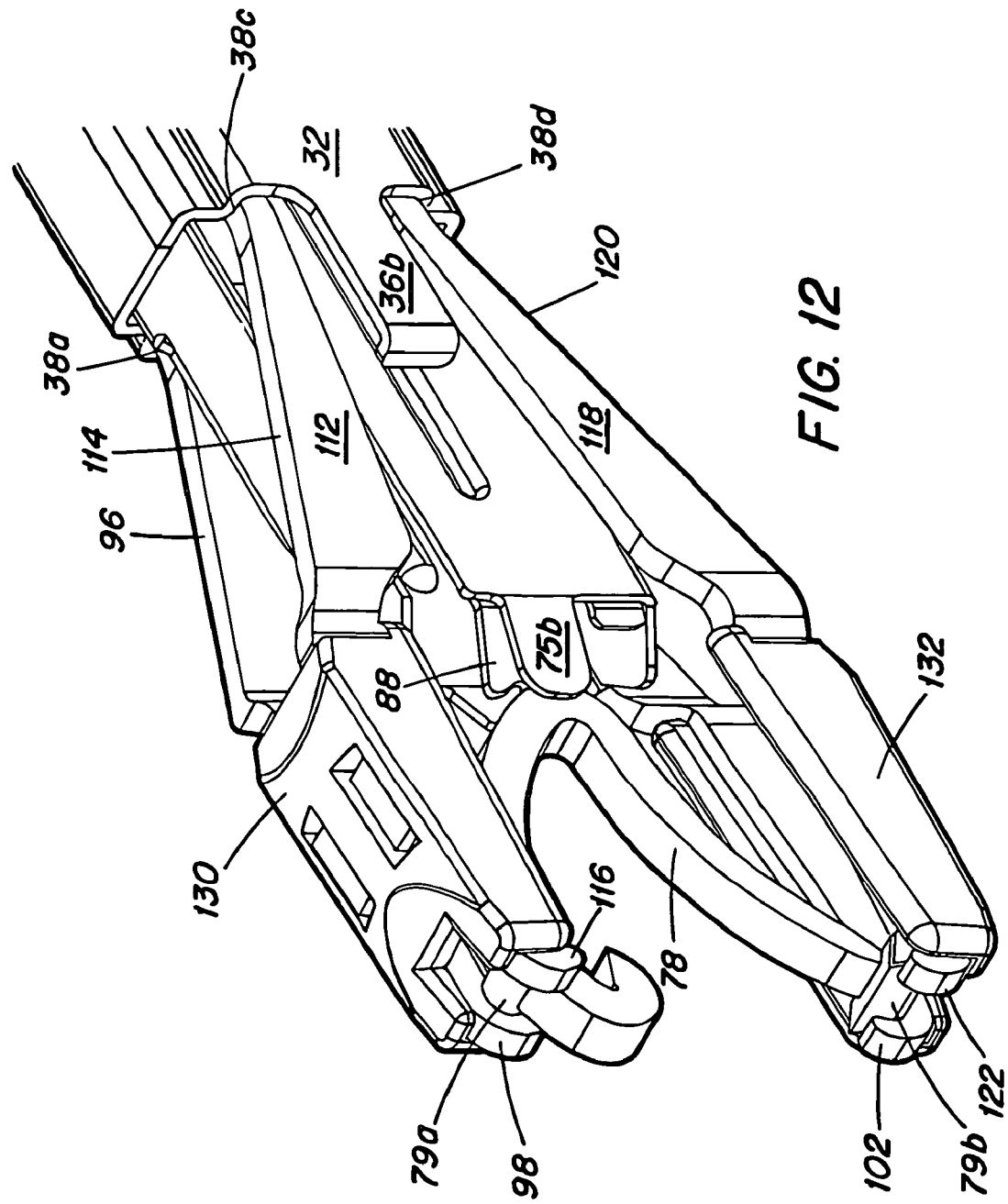
FIGS. 12-14 are sequential, perspective views of the jaw assembly during the process of closing a clip.

According to one embodiment, clip applier 10 is configured such that further actuation of trigger 144 (FIGS. 6 and 7) functions to open a clip 78 disposed in jaw assembly 90. Clips 78 are fed through clip channel 72 in a compressed configuration, which reduces the required diameter of shaft assembly 22. The most distal clip 78 is fed into jaw assembly 90 in the same compressed configuration. As illustrated in FIG. 12, first arm 98, second arm 102, third arm 116 and fourth arm 122 of respective first leg 94, second leg 99, third leg 112 and fourth leg 118 of jaw assembly 90 include respective catch structures such as first hook 98A, second hook 102A, third hook 116A and fourth hook 122A. Hooks 98A, 102A, 116A, 122A limit the forward motion of clip 78 in jaw assembly 90. Therefore, when further pressure is applied to the rear of clip 78 via feeder tab 88 of feeder bar 80, the force is translated through the legs of clip 78, which causes jaw assembly 90 (and clip 78 contained therein) to open wider. The width to which jaw assembly 90 can be opened may be limited by the cam surfaces 38A-38D of collar 32.

Figure 11:
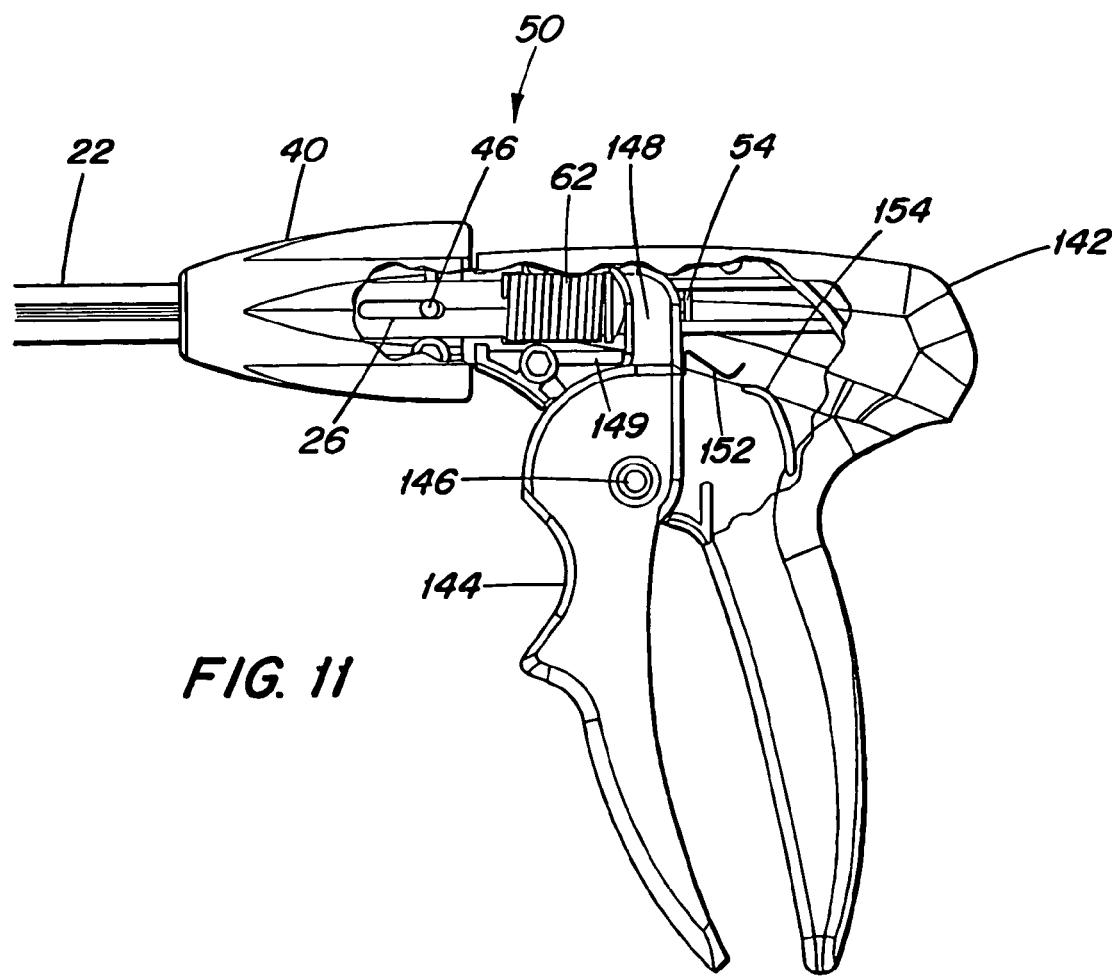
FIG. 11 is a partial cut-away view of a handle assembly in accordance with an embodiment of the subject matter disclosed herein.

Following completion of the feed stroke, further actuation of the trigger 144 actuates jaw assembly 90. FIG. 11 is a side cut-away view of the proximal end of clip applier 10 with the device in a fully actuated state. Pin 46 is always in clearance with channel 26 in shaft member 22. A rib 149 in handle body 142 limits the forward motion of claw 148 of trigger 144, and hence limits the forward motion of yoke 50.

Figure 13:
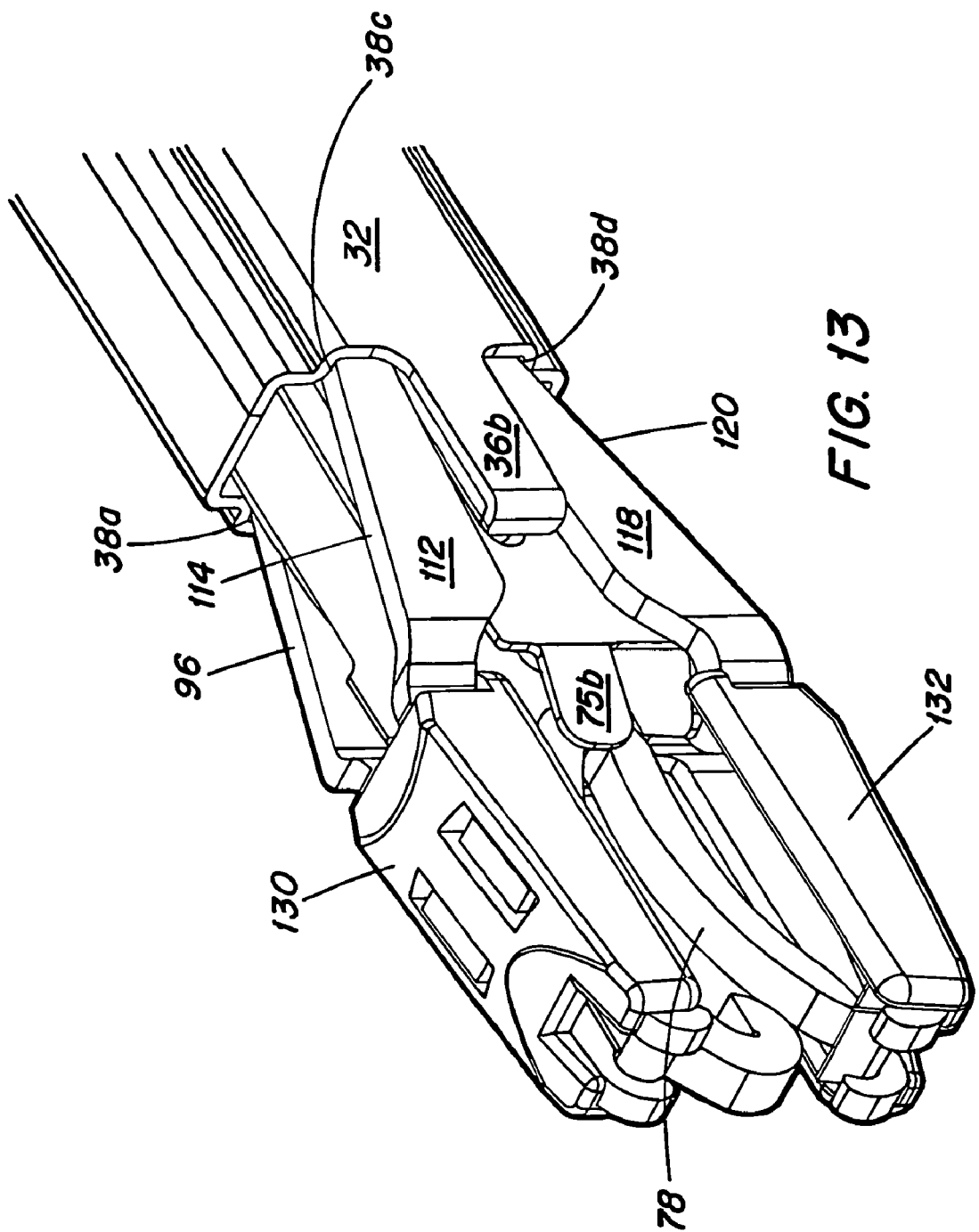
Figure 14:
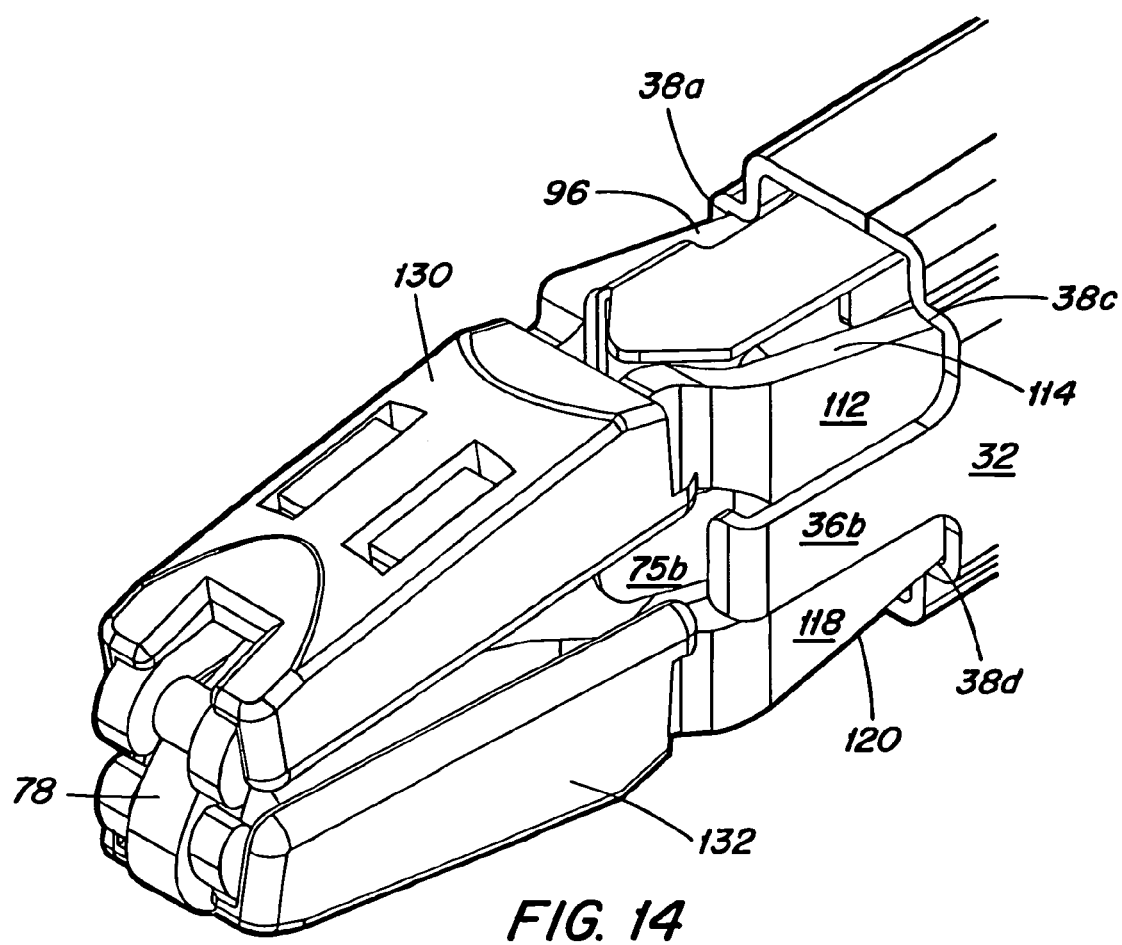

FIGS. 12-14 are perspective views of distal end of clip applier 10 illustrating jaw assembly 90 while it is being closed. Referring first to FIG. 12, following completion of the feed portion of the stroke, a clip 78 is positioned in jaw assembly 90, which is in an open configuration. According to one embodiment, the second portion of the stroke of trigger 144 closes jaw assembly 90. More particularly, referring to FIGS. 13-14, the second portion of the stroke moves outer shaft 22 in a distal direction relative to fixed grip 142 (FIG. 1), knob 40 (FIG. 1), and clip channel 72 (FIGS. 2B and 2C). As the outer shaft 22 and collar 32 are moved in a distal direction, cam surfaces 38A-38D of collar 32 impinge on cam surfaces 96, 100, 114, 120, closing jaw assembly 90. The use of four separate cams reduces the likelihood of scissoring as jaw assembly 90 is closed.

While jaw assembly 90 is closing, feeder tab 88 (FIG. 12) of feed bar 80 remains in contact with the rear of clip 78. Closing jaw assembly 90 tends to drive the rear of clip 78 in a proximal direction, which increases the pressure between feeder tab 88 and clip 78 in jaw assembly 90, thereby enhancing the stability of clip 78 in jaw assembly 90. This enhanced clip stability is particularly advantageous when a surgeon is pushing a clip 78 onto a vessel.

Additional features of clip applier 10 will be explained with reference to FIGS. 12-15. Each jaw arm 98, 102, 116, 122 terminates in a hook 98A, 102A, 116A, 122A, respectively. Hooks 98A and 116A of first jaw arm 98 and third jaw arm 116 cooperate to retain boss 79A of clip 78 in jaw assembly 90. Similarly, hooks 102A and 122A of second jaw arm 102 and fourth jaw arm 122 cooperate to retain boss 79B of clip 78 in jaw assembly 90. This configuration of jaw assembly 90 provides four distinct points of contact between jaw assembly 90 and clip 78, which reduces the likelihood of jaw assembly 90 scissoring while it is closing. In addition, this configuration permits the force applied by jaw assembly 90 to be applied to the distal end of clip 78, which facilitates locking clip 78. The rear (i.e., proximal) portion of clip 78 is retained between tabs 75A, 75B extending from the distal end of clip channel 72, which limits the range of lateral motion available to clip 78. In addition, feed tab 88 (FIG. 12) of feed bar 80 prevents the rear (i.e., proximal) portion of clip 78 from being pushed back into clip channel 72 when clip 78 is being applied. Accordingly, clip 78 is maintained stable in three dimensions while retained in jaw assembly 90.

According to one embodiment, only a portion of ratchet guide 154 (FIGS. 5 and 11) includes ratchet teeth. Preferably the length of ratchet guide 154 having teeth corresponds to the feed portion of the actuation stroke of trigger 144. Reversing the direction of feeder bar 80 during the feed stroke may cause clip 78 to become unstable, or even to fall out of jaw assembly 90. The teeth on ratchet guide 154 inhibit feeder bar 80 from being moved in a proximal direction during the feed stroke. A second portion of ratchet guide 154, which preferably corresponds to the portion of the stroke during which jaw assembly 90 is closed, permits yoke 50 and outer shaft 22 to move freely in the distal direction and the proximal direction. This allows a user to "approximate" a clip 78 during the closing process, i.e., to partially close a clip 78 then to re-open jaw assembly 90 to reposition a clip 78, if necessary.

In one embodiment, distal collar keys 36A, 36B provide a stop to prevent jaw assembly 90 from unintended closings during use, e.g., under compression as may be incurred during use in the body. Referring to FIG. 13, it can be seen that the distal portion of collar keys 36A, 36B include an inwardly-turned segment positioned to block leg members 112 and 118 from closing. However, leg members 94, 99, 112, and 118 taper inwardly near the distal end of jaw assembly 90. Therefore, as illustrated in FIG. 14, when outer shaft 22 is advanced, collar keys 36A, 36B advance past the respective tapers in leg members 94, 99, 112 and 11 8, allowing jaw assembly 90 to close. Additionally, collar keys 36A, 36B function as cams to facilitate re-opening jaw assembly 90 after the device is actuated and outer shaft 22 retracts.

FIG. 14 illustrates jaw assembly 90 in a substantially closed configuration. Further actuation of jaw assembly 90 will lock clip 78. The distal motion of outer shaft 22 compresses knob spring 64 (FIGS. 2B and 2C) between flange 24A, 24B (FIGS. 2B and 2C) and the interior distal edge of knob 40 (FIGS. 2B and 2C), which provides the bias force to return trigger 144 and outer shaft 22 to their unactuated states (FIG. 6). After jaw assembly 90 is closed, the user may release trigger 144, and the bias force provided by knob spring 64 urges outer shaft 22 and feeder bar 80 in a proximal direction. This "resets" clip applier 10 back to an unactuated state so that another clip may be fed to jaw assembly 90.

During the reset sequence, tabs 76 (FIG. 20) on clip channel 72 inhibit clips 78 in channel 72 from moving in the proximal direction. Tabs 84 (FIG. 19) on feeder bar 80 move across clips 78 in clip channel 72 and snap into position behind the bosses of clips 78. As feeder bar 80 moves proximally, foot member 89 of feeder bar 80 contacts boss 79B (FIG. 12) of the most distal clip 78 in clip channel 72, causing clip 78 to rotate. Rotation of the most distal clip 78 stops when boss 79A (FIG. 12) contacts the most distal tab 84 of feeder bar 80, which preferably positions the rear of clip 78 substantially in the center of clip channel 72. As feeder bar 80 continues to move proximally, feed tab 88 is positioned adjacent the rear of the most distal clip 78, ready for the next actuation cycle.

Figure 15A:
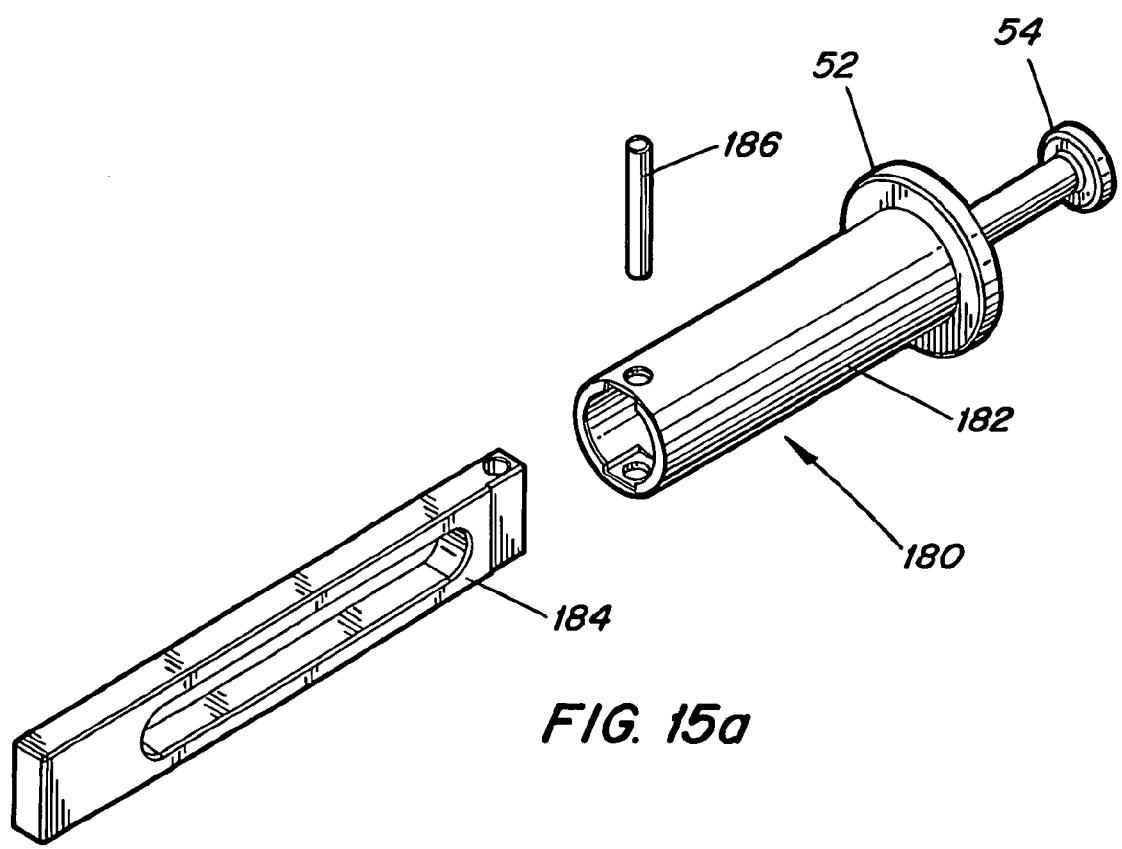
FIGS. 15A-15C are perspective views of an alternate embodiment of a yoke in accordance with the subject matter disclosed herein.
Figure 15B:
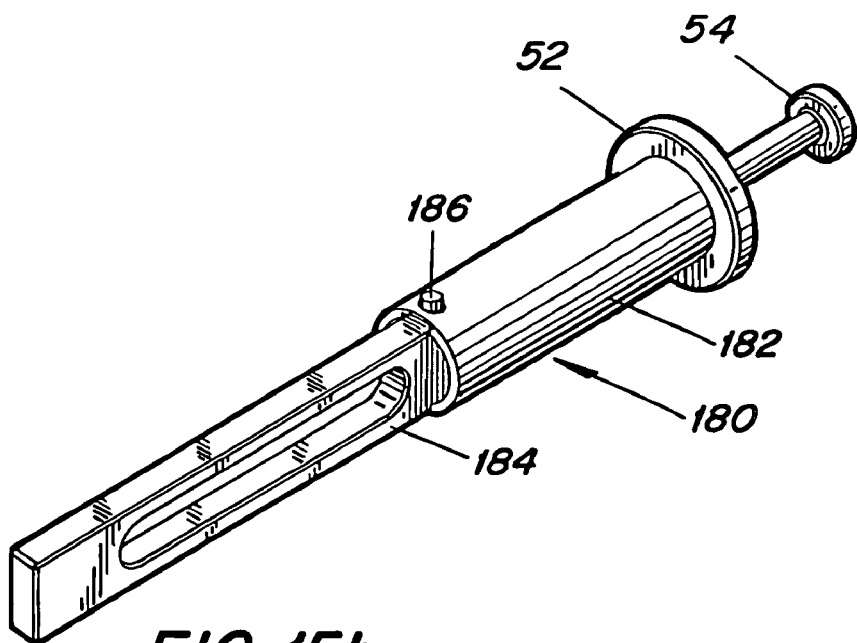
Figure 15C:
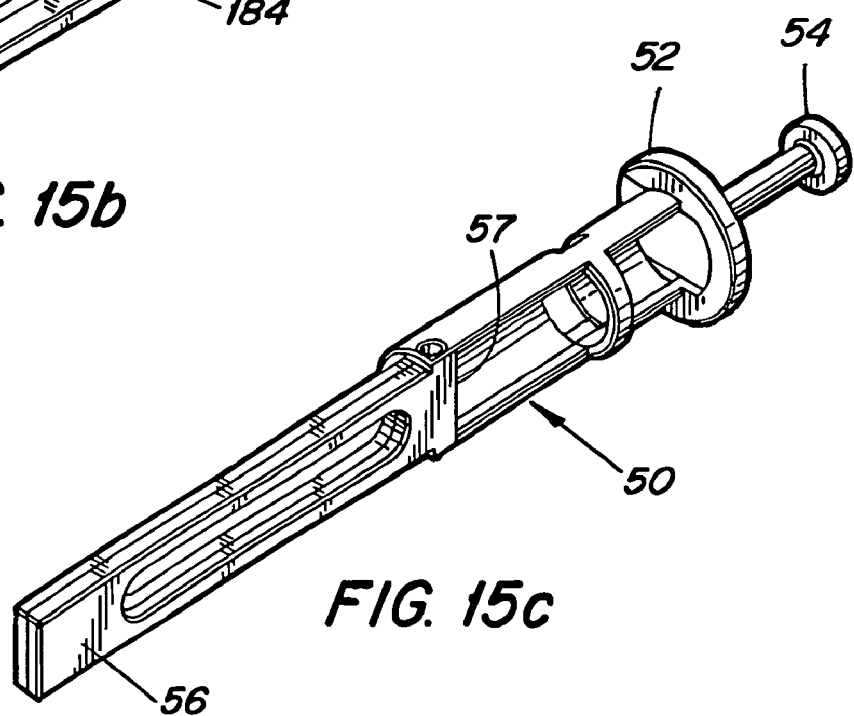

FIGS. 15A-15B illustrate alternate embodiments of a yoke in accordance with the subject matter disclosed herein. FIG. 15A is a perspective view of an alternate embodiment of a two-part yoke, generally designated 180, prior to assembly, and FIG. 15B is a perspective view of yoke 180 after assembly. Yoke 180 includes a first body portion 182 and a second body portion 184 connected by a pin 186. Feeder spring 60 (FIG. 6) may be disposed entirely within first body portion 182 of yoke 180. In other respects, yoke 180 is substantially similar to yoke 50. Advantages of a two-piece yoke 180 as depicted in FIGS. 15A-15B include better retention of feeder spring 60 within the body of yoke 180 and ease of assembly. FIG. 15C is a perspective view of yoke 50 depicted in FIG. 2, but from the opposite side to illustrate interior distal edge 57 that receives tab 86 (FIGS. 2B and 2C) of feeder bar 80.

Figure 16:
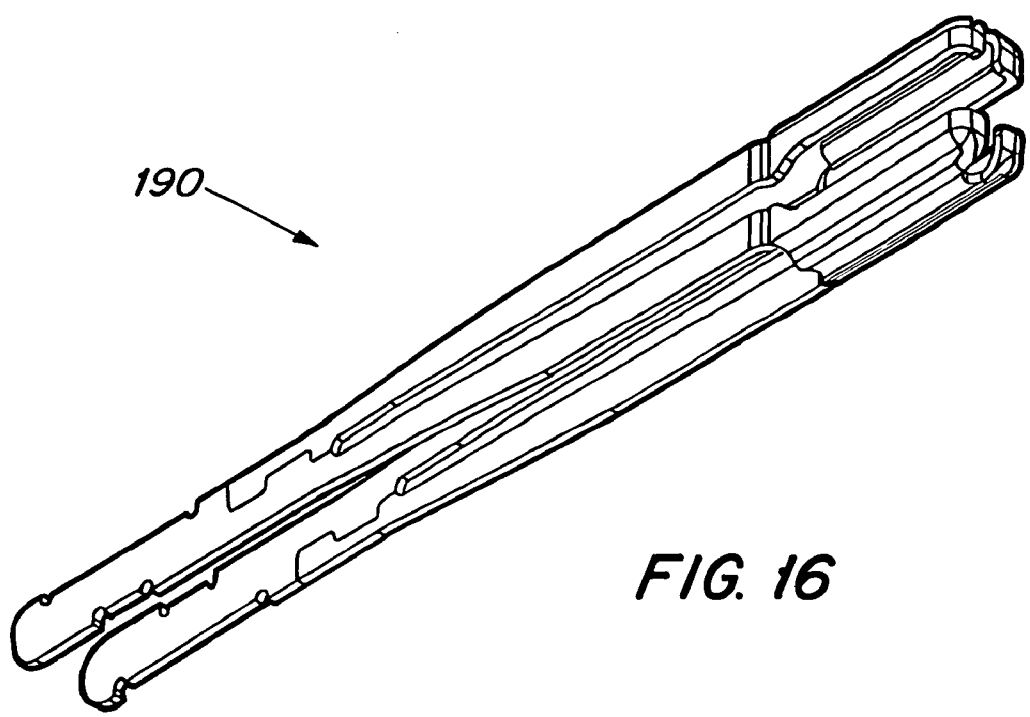
FIG. 16 is a perspective view of an alternative embodiment of a jaw assembly in accordance with the subject matter disclosed herein.
Figure 17:
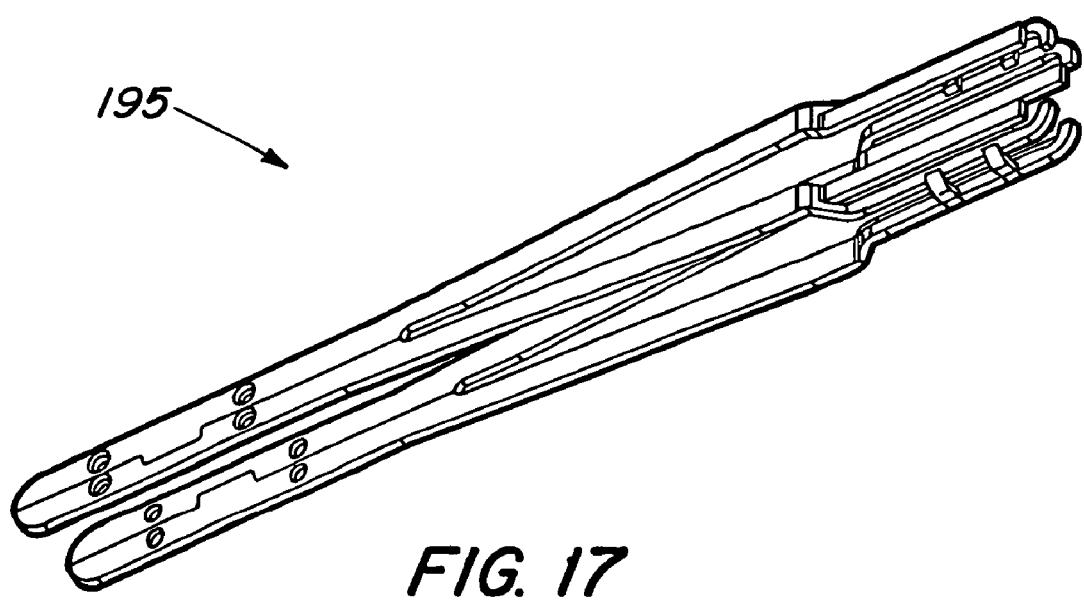
FIG. 17 is a perspective view of another alternative embodiment of a jaw assembly in accordance with the subject matter disclosed herein.

FIGS. 16-17 are perspective views of alternate embodiments of jaw assemblies, generally designated 190 and 195, respectively, in accordance with the subject matter disclosed herein. The jaw assemblies 190 and 195 depicted in FIGS. 16-17 are substantially similar to jaw assembly 90, but are particularly advantageous when used with a clip applier J10 having a shaft assembly 20 with a smaller diameter, e.g., 5 millimeters. The principal distinction between jaw assemblies 190 and 195 depicted in FIGS. 16-17 and jaw assembly 90 is the elimination of bridge members 104,124 (FIG. 2C) in favor of making each jaw member a discrete component.

Figure 21:
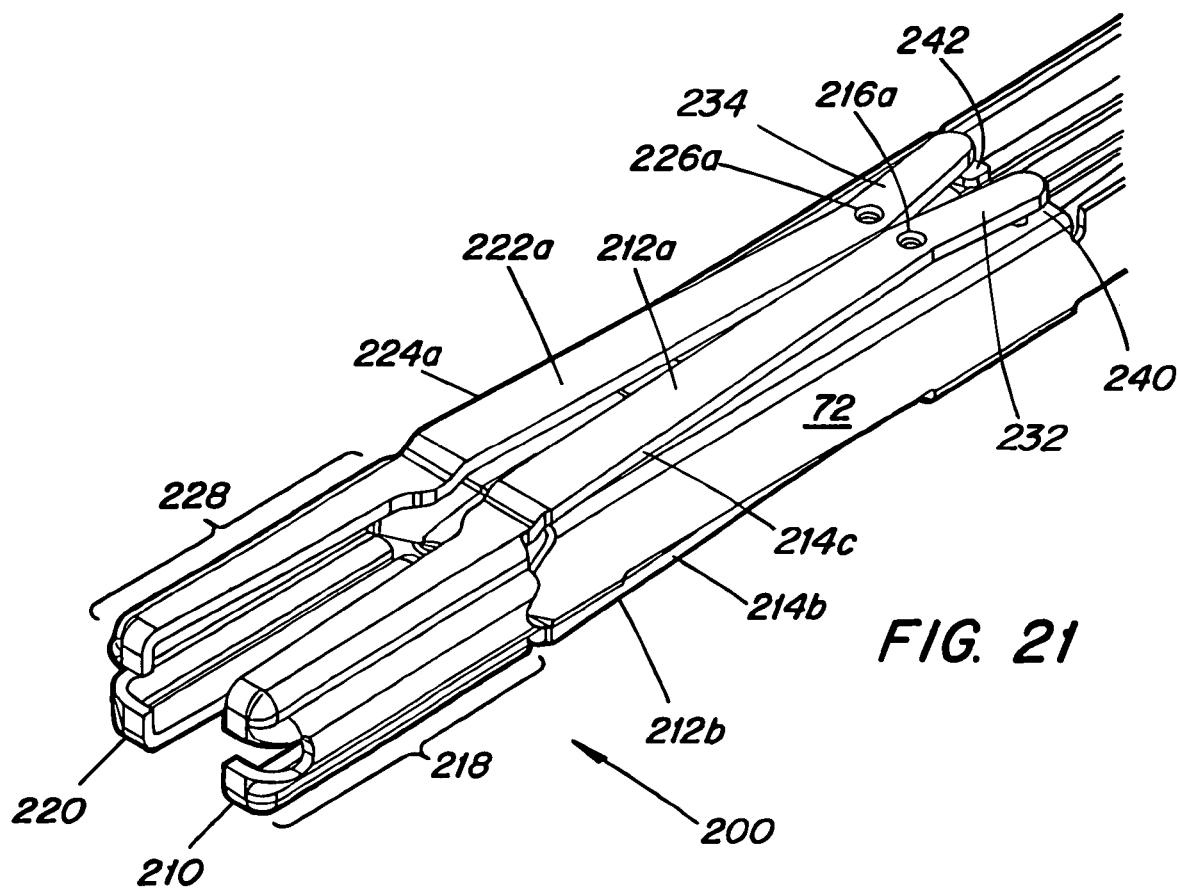
FIG. 21 is a perspective view of yet another alternate embodiment of a jaw assembly in accordance with the subject matter disclosed herein.
Figure 26A:
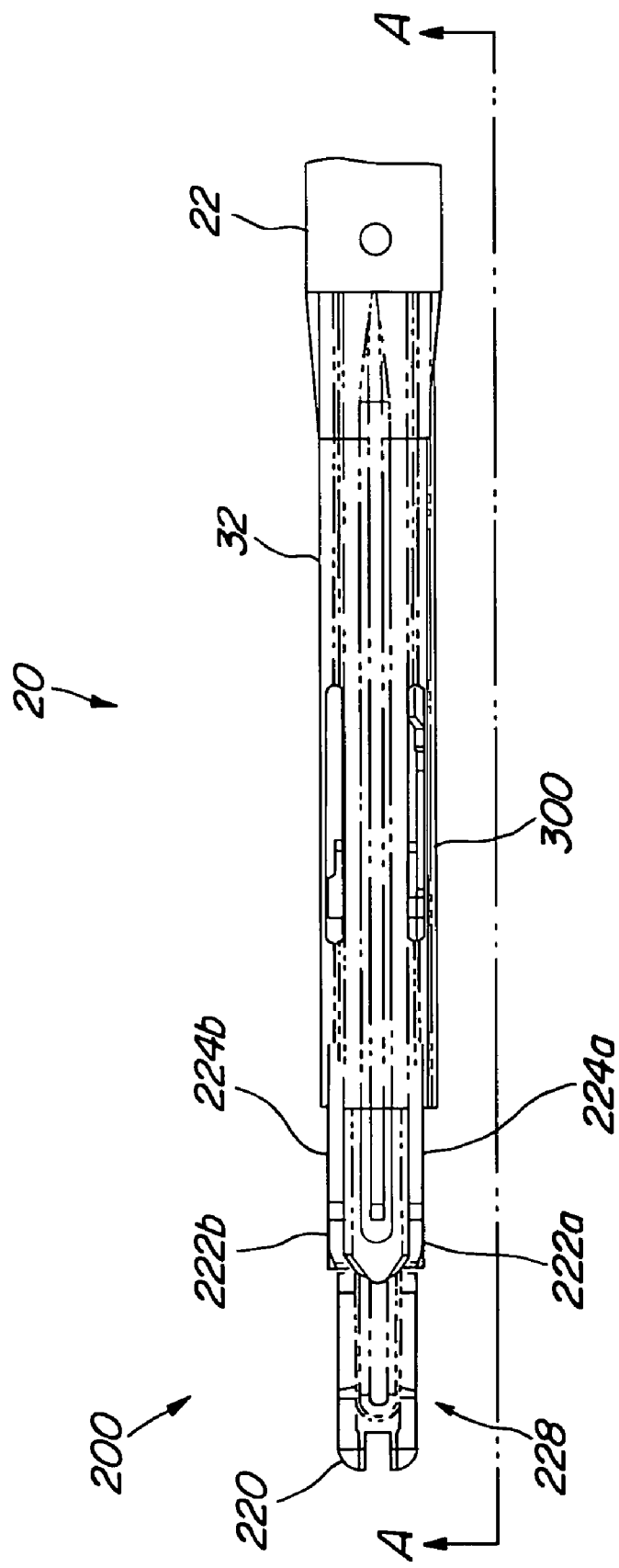
FIG. 26A is a top plan view of a distal portion of a clip applier including a jaw opening member in accordance with the subject matter disclosed herein, illustrating a jaw assembly of the clip applier in a rest position.

FIGS. 21-24 are perspective views of the distal end of a clip applier, such as clip applier 10 as described above, illustrating an alternative embodiment of a jaw assembly, generally designated 200. FIG. 21 illustrates the distal end of clip applier 10 with collar or collar portion 32 removed to better illustrate jaw assembly 200. Jaw assembly 200 includes a first jaw member 210 and a second jaw member 220. First jaw member 210 includes a leg member 212A and a proximal end member 232 connected to clip channel 72 at a pivot point 216A. First jaw member 210 also includes a leg member 212B and an associated proximal end member (not visible) connected to clip channel 72 at a pivot point (not visible) on the opposite side of clip channel 72. Each leg member 212A, 212B has a respective outer cam surface 214A, 214B. The distal end of the portion of jaw assembly 200 that includes first jaw member 210 forms a first jaw 218. Second jaw member 220 may be substantially identical to first jaw member 210. Second jaw member 220 thus includes a leg member 222A and a proximal end member 234 connected to clip channel 72 at a pivot point 226A. Although not visible in FIG. 21, second jaw member 220 also includes another leg member 222B (see FIG. 26A) and proximal end member connected to clip channel 72 at a pivot point on the opposite side of clip channel 72. Leg member 222A has a cam surface 224A and leg member 222B (FIG. 26A) similarly has a cam surface 224B (FIG. 26A). The distal end of the portion of jaw assembly 200 that includes second jaw member 220 forms a second jaw 228. In some embodiments, tabs 240, 242 extend from the surface of clip cartridge 72 on one or both sides thereof and function as cams to bias the respective proximal ends of jaw legs 212A, 222A and/or 212B, 222B outwardly. This tends to bias jaw assembly 200 toward a closed configuration.

Figure 22:
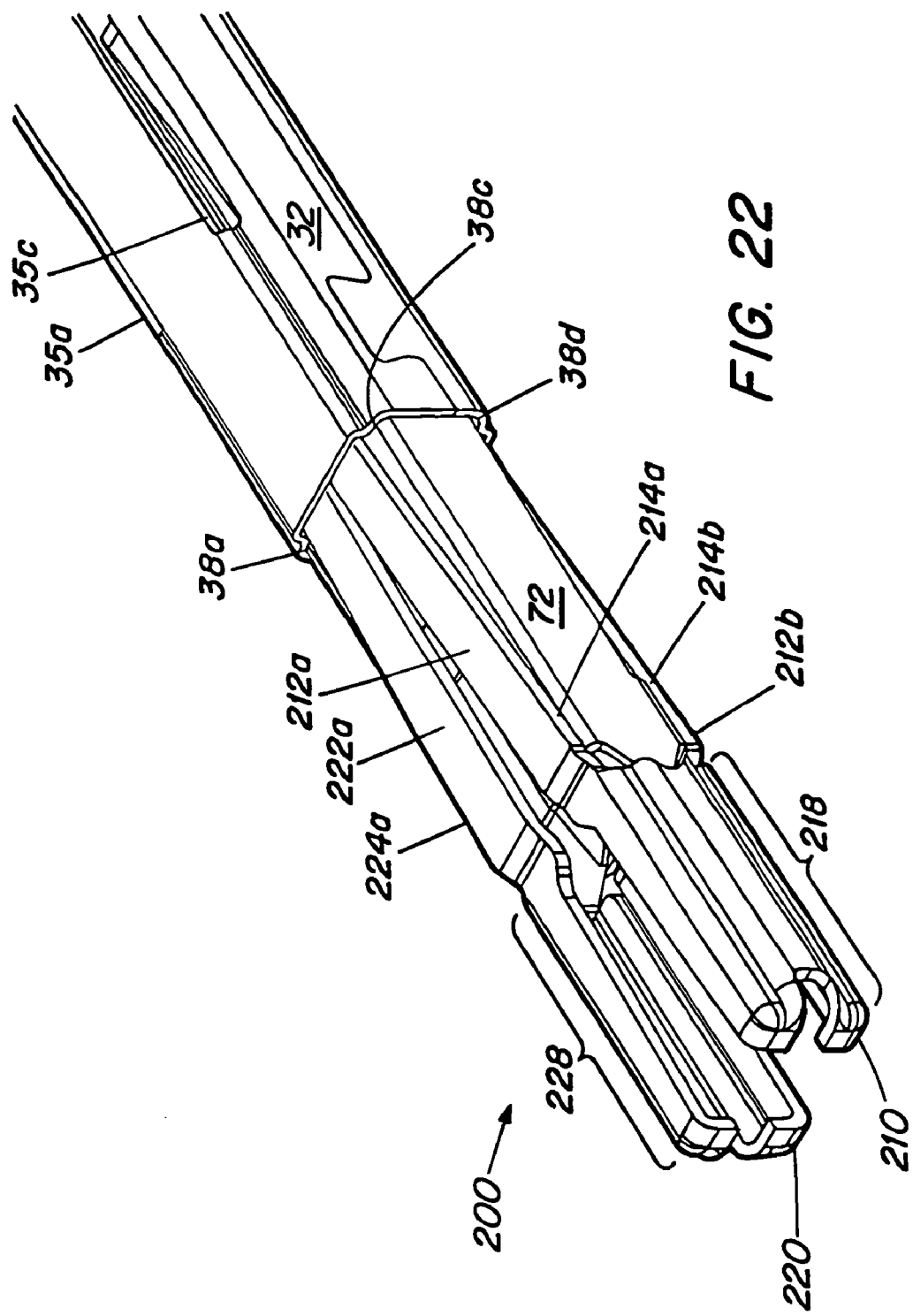
FIG. 22 is a perspective view of the jaw assembly illustrated in FIG. 21 in a clip feed position.
Figure 23:
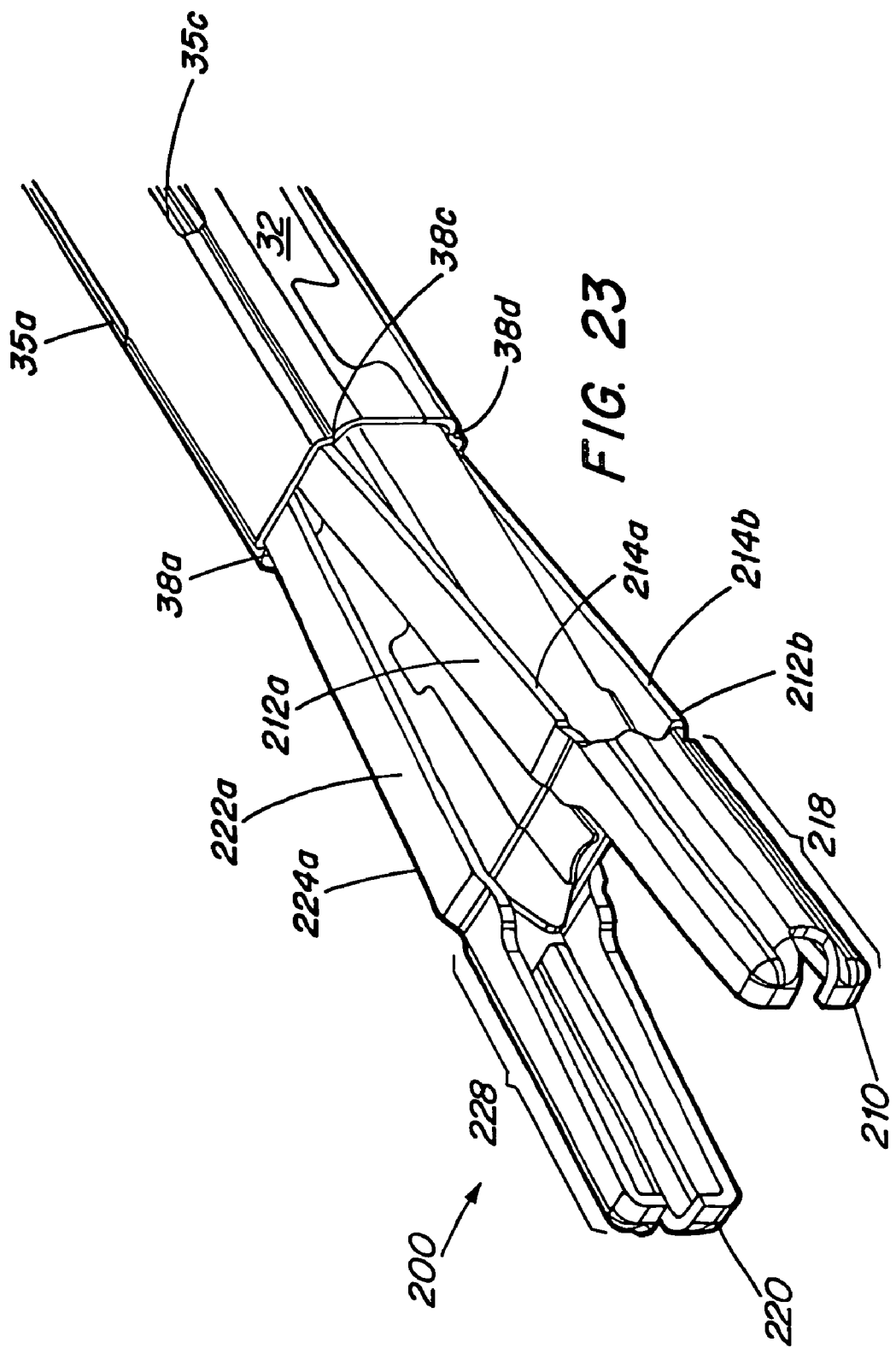
FIG. 23 is a perspective view of the jaw assembly illustrated in FIG. 21 in an open position.
Figure 24:
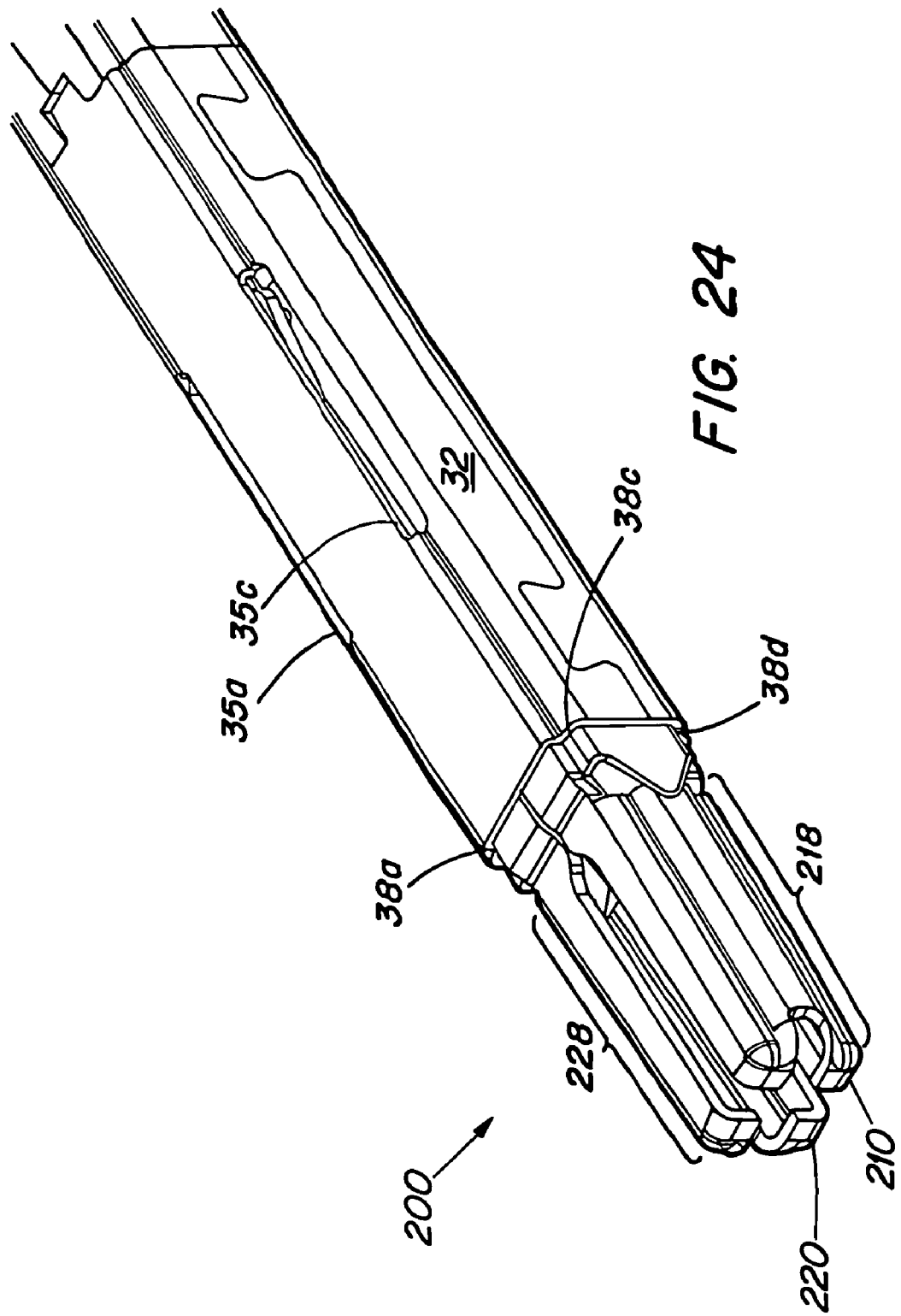
FIG. 24 is a perspective view of the jaw assembly illustrated in FIG. 21 in a closed position.

It will be appreciated that jaws 218, 228 may be opened and closed by pivoting jaw members 210, 220 about respective pivot points 216A, 226A, and the opposing pivot points not visible in FIG. 21. FIGS. 22-24 are sequential views of the distal end of clip applier 10 that illustrate closing jaw assembly 200. FIG. 22 depicts jaw assembly 200 in the clip feed or "jaw set" position, in which jaws 218, 228 preferably are substantially aligned with surfaces of clip channel 72 to facilitate the smooth transfer of a clip 78 from clip channel 72 into jaw assembly 200. Collar 32 limits the outward motion of the proximal ends (e.g., proximal end members 232 and 234 shown in FIG. 21) of jaw legs 212A, 222A, 212B, 222B, which preferably are dimensioned such that jaw assembly 200 is at rest as depicted in FIG. 22.

FIG. 23 depicts jaw assembly 200 in an open configuration. As discussed above, driving a clip 78 forward in jaw assembly 200 will open jaw assembly 200 (clip 78 is omitted in FIG. 23 for clarity of illustration). The opening of jaw assembly 200 is limited by contact between cam surfaces 214A, 214B and 224A, 224B of jaw members 210 and 220 and corresponding cam surfaces 38A-38D of collar 32.

FIG. 24 depicts the jaw assembly 200 in a closed configuration. As described above in connection with FIGS. 12-14, when collar 32 is advanced, cams 38A-38D impinge on cam surfaces 214A, 214B, 224A, 224B, which closes the jaw assembly 200. Collar 32 includes slots (e.g., slots 35A and 35C and opposing slots not visible) that allow the proximal end members (e.g., proximal end members 232 and 234 shown in FIG. 21) of jaw legs 212A, 222A, 212B, 222B to extend outwardly so that jaws 218, 228 can close.

Figure 25:
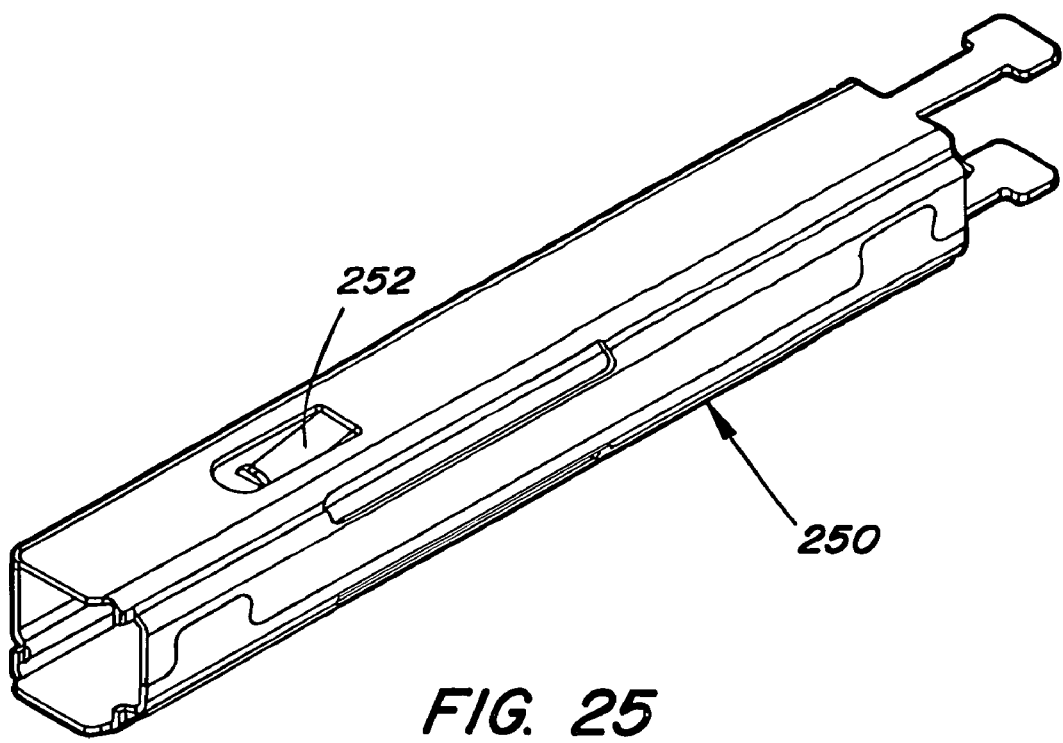
FIG. 25 is a perspective view of an alternate embodiment of a collar in accordance with the subject matter disclosed herein.

FIG. 25 depicts an alternate embodiment of a collar, generally designated 250, that is particularly adapted for use with jaw assembly 200 depicted in FIGS. 21-24. Collar 250 is substantially similar to the collar 32 depicted in FIGS. 21-24, and includes a tab 252 that extends into the chamber defined by the collar 250 to prevent jaw members 210, 220 from unintended closing, e.g., due to pressure inside the body cavity. When jaw assembly 200 is in the unactuated position or the partially-actuated position, tab 252 fits between leg members 212A, 222A to prevent jaw assembly 200 from closing. By contrast, when jaw assembly 200 is fully actuated, tab 252 moves distally, allowing jaw assembly 200 to close.

Figure 28A:
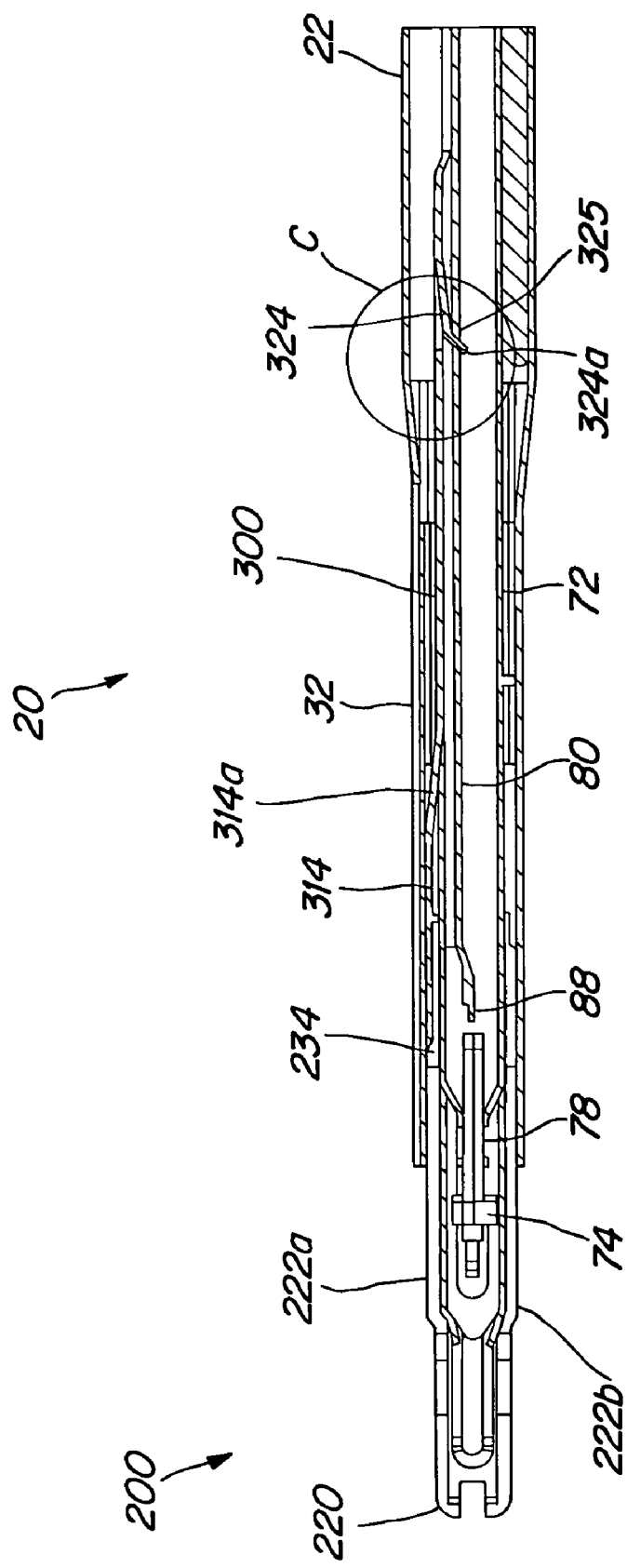
FIG. 28A is a cutaway inside view of the clip applier in a position corresponding to that shown in FIG. 26A.
Figure 28B:
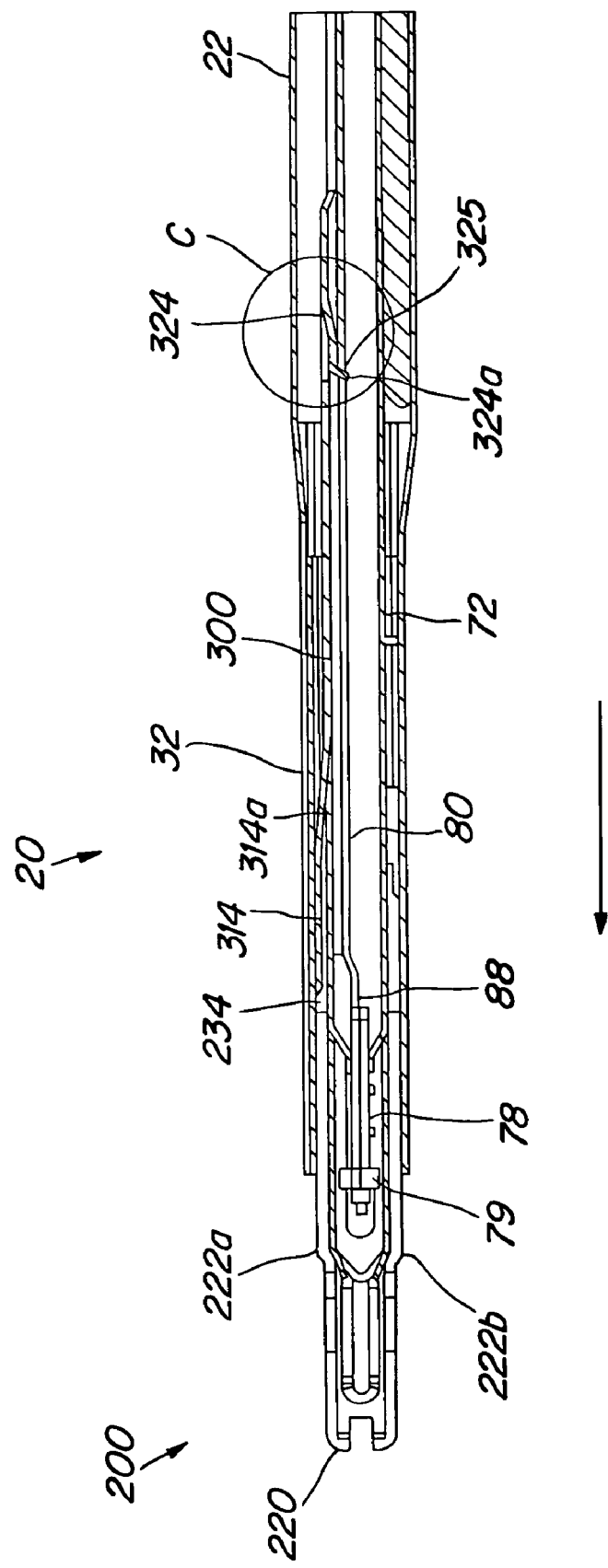
FIG. 28B is a cutaway inside view of the clip applier in a position corresponding to that shown in FIG. 26B.
Figure 28C:
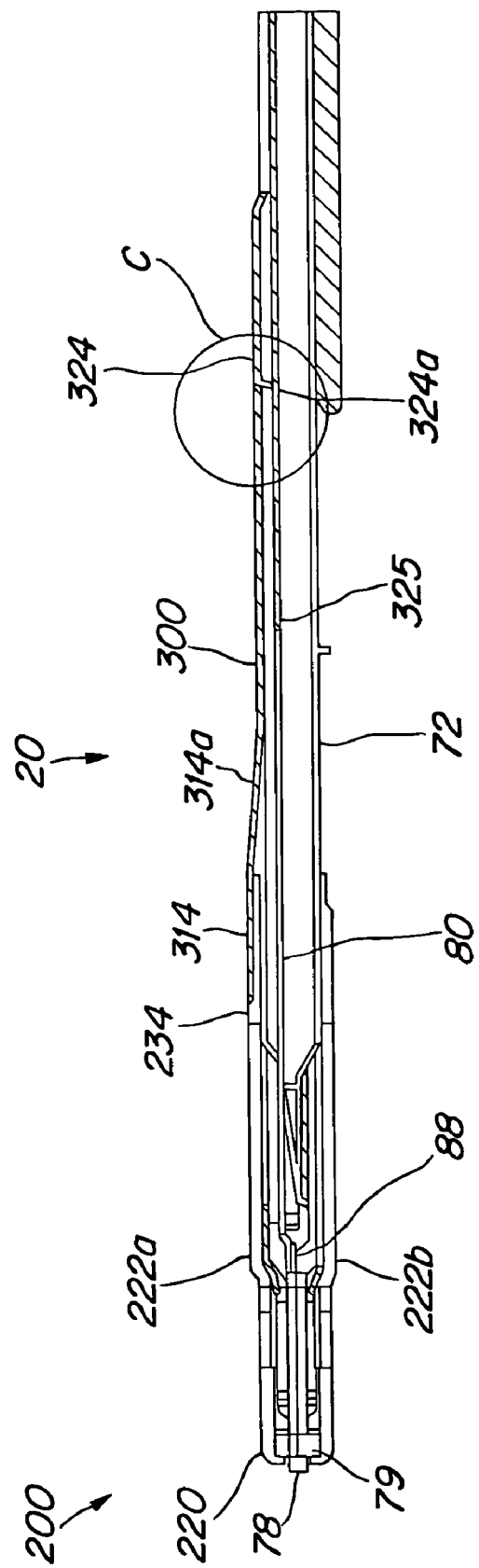
FIG. 28C is a cutaway inside view of the clip applier in a position corresponding to that shown in FIG. 26C.
Figure 29A:
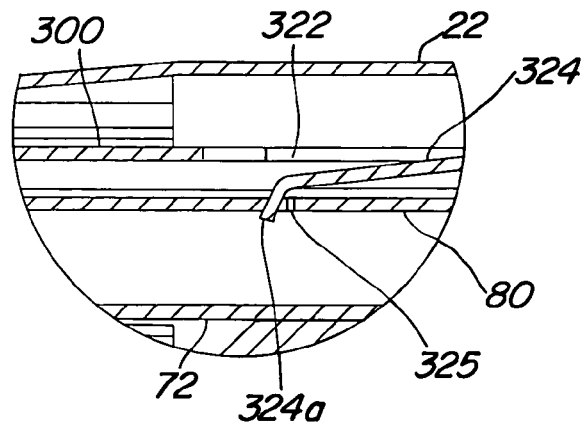
FIG. 29A is a detailed view of a portion of the clip applier illustrated in FIG. 28A, showing the interaction between the jaw opening member and the clip feeding bar.
Figure 29B:
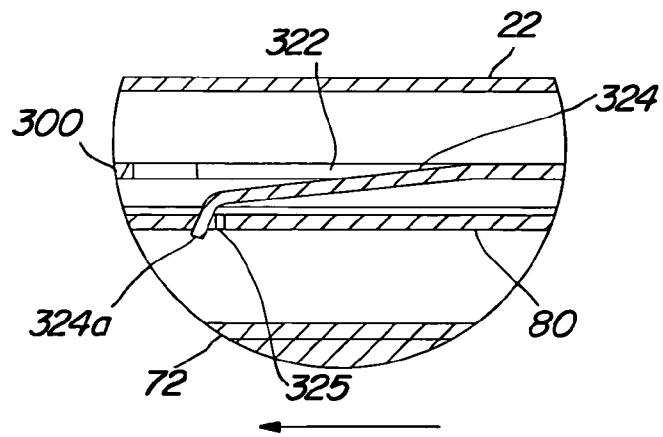
FIG. 29B is a detailed view of a portion of the clip applier illustrated in FIG. 28B, showing the interaction between the jaw opening member and the clip feeding bar.
Figure 29C:
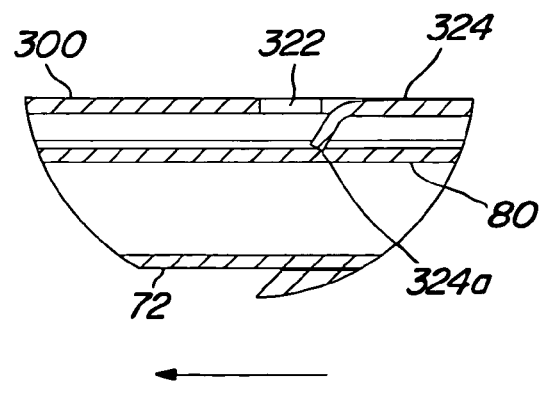
FIG. 29C is a detailed view of a portion of the clip applier illustrated in FIG. 28C, showing the interaction between the jaw opening member and the clip feeding bar.
Figure 30:
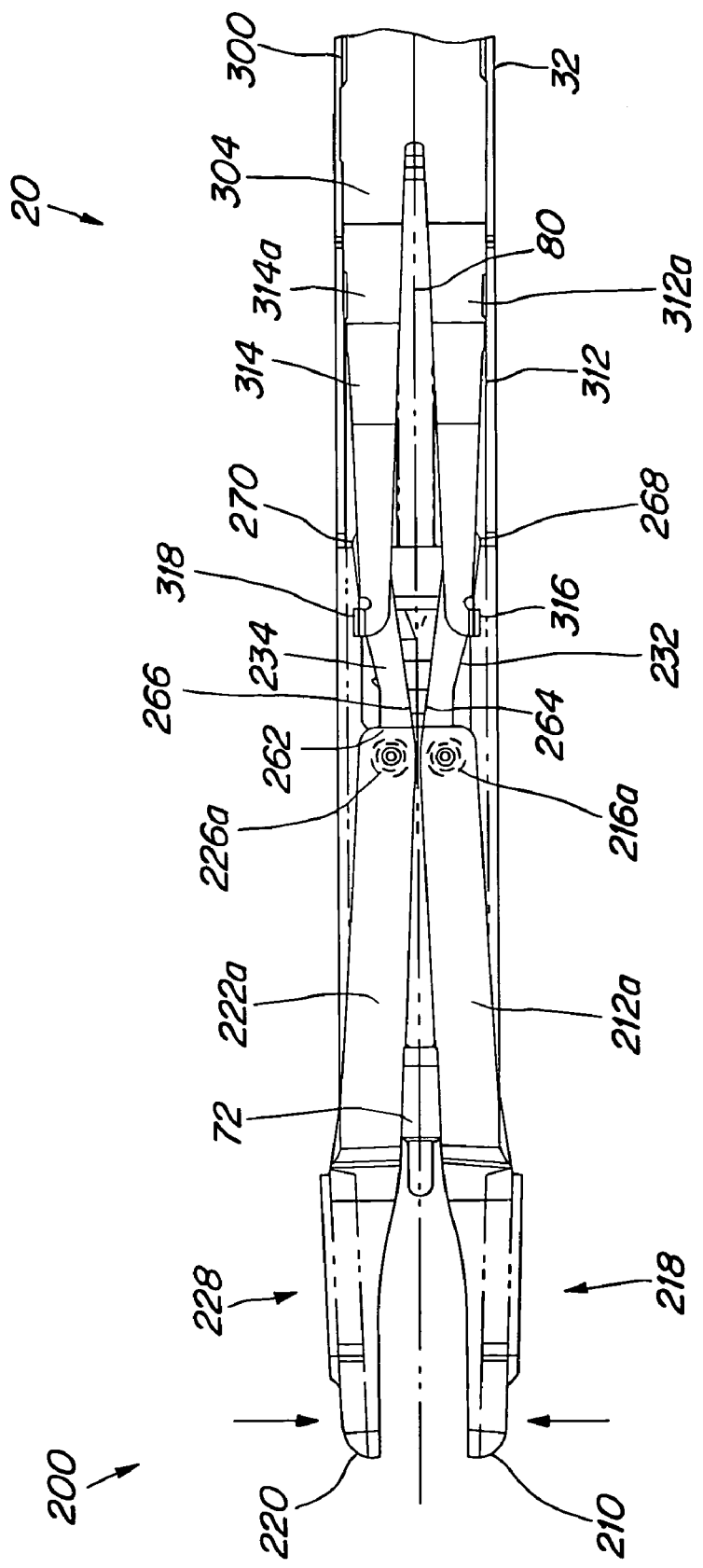
FIG. 30 is a cutaway side elevation view of the clip applier in a reset position, showing an interaction between the jaw opening member and the jaw assembly.

Referring now to FIGS. 26A-30, another embodiment of clip applier 10 is illustrated in which a jaw opening member 300 has been incorporated. FIGS. 26A, 27A, 28A, and 29A generally correspond to a "rest" position of clip applier 10. The "rest" position can correspond to the end of the return stroke or the beginning of the forward stroke of clip applier 10, after jaw assembly 200 has reached full aperture and a clip 78 has been released therefrom. FIGS. 26B, 27B, 28B, and 29B generally correspond to a "jaw set" position of clip applier 10, in preparation for feeding a clip 78 into first and second jaws 218 and 228 as described previously. FIGS. 26C, 27C, 28C, and 29C generally correspond to a feeding position of clip applier 10, in which a clip 78 is being fed into first and second jaws 218 and 228 and just prior to first and second jaws 218 and 228 opening to full aperture. FIGS. 26A-26C illustrate a top plan view of clip applier 10, and specifically of jaw assembly 200 and the distal portion of outer shaft 22 that includes collar portion 32. FIGS. 27A-27C illustrate a side elevation view of clip applier 10, as viewed from the perspective of line A-A indicated in FIGS. 26A-26C, with portions of outer shaft 22 and collar portion 32 removed to provide a clear view of jaw opening member 300 and its interaction with jaw assembly 200. FIGS. 28A-28C illustrate a cut-away view of clip applier 10 taken along line B-B indicated in FIGS. 27A-27C, providing a view generally of the inside of a top section of clip applier 10 from the vantage point of the central longitudinal axis of jaw assembly 200 and shaft assembly 20 generally coincident with line B-B. FIGS. 29A-29C illustrated an enlarged view of section detail C shown in FIGS. 28A-28C. FIG. 30 illustrates a reset position of clip applier 10.

As will become evident from the following description, in connection with the description hereinabove of the general operation of clip applier 10 in its various embodiments, jaw opening member 300 interacts with jaw assembly 200 to increase the jaw aperture generally defined by the opening between first and second jaw members 210 and 220, and thereby to improve the ability of clip applier 10 to release a clip 78 from first and second jaw members 210 and 220 at the time intended by the user. For instance, the operation of jaw opening member 300 can reduce the risk that one or more bosses of clip 78 snag or hang up on one or more of the surfaces of jaw assembly 200 with which clip 78 contacts. Generally, the increase in the jaw aperture will occur during the beginning and end of the stroke of clip applier 10, which corresponds roughly to the time at which a clip 78 is released from jaw assembly 200 after having been applied to a target tissue of a surgical site.

As shown in the various views of FIGS. 26A-30, jaw opening member 300 is disposed within outer shaft 22. Jaw opening member 300 extends far enough into collar portion 32, and generally on one side of outer shaft 22 and collar portion 32, so as to interact with at least two opposing leg members of jaw assembly 200, which are designated hereinafter as first leg member 212A and second leg member 222A (see, e.g., FIG. 27A).

Figure 27A:
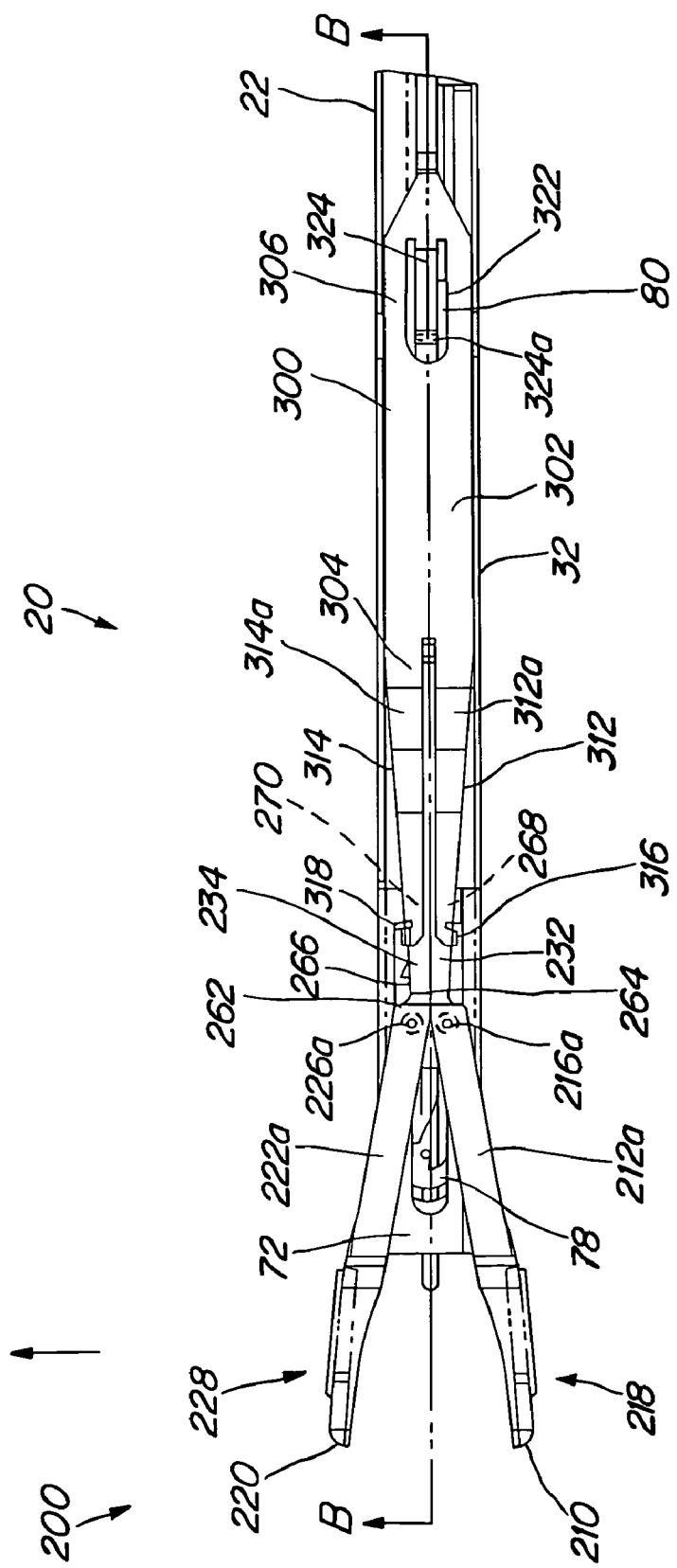
FIG. 27A is a cutaway side elevation view of the clip applier in a position corresponding to that shown in FIG. 26A.

Referring to FIGS. 27A and 30, jaw opening member 300 is disposed generally adjacent to feeder bar 80. Jaw opening member 300 includes a main portion or body 302, a distal portion 304 nearest to jaw assembly 200, and a proximal portion 306 farthest from jaw assembly 200. Distal portion 304 is bifurcated into a first arm 312 and a second arm 314 such that first and second arms 312 and 314 can act as spring members. First arm 312 terminates at a first finger or extension 316, and second arm 314 terminates at a second finger or extension 318. First finger 316 and second finger 318 are directed generally inwardly into the interior of collar portion 32. By this configuration, distal portion 304 of jaw opening member 300 straddles first and second proximal end members 232 and 234 of first and second jaw members 210 and 220, respectively, thereby enabling first and second fingers 316 and 318 to respectively engage the portions of the outer surfaces of first and second jaw members 210 and 220 corresponding to first and second proximal end members 232 and 234.

As shown in FIG. 27A, proximal portion 306 of jaw opening member 300 includes a cut-out section 322 in which a tab 324 is formed. Tab 324 is angled inwardly for contacting feeder bar 80. As shown in FIG. 28A and in greater detail in FIG. 29A, tab 324 terminates at an end portion 324A that is angled inwardly to a greater degree than the remaining portion of tab 324. End portion 324A facilitates the engagement of tab 324 with a tab aperture 325 formed in feeder bar 80, as described below.

It will be noted from the description herein that the jaws are spring loaded so as to be normally biased closed. Jaw opening member 300 acts to override the spring in a manner described herein In accordance with the present embodiment, it can be seen from FIGS. 27A and 30 that an interfacial region is formed in jaw assembly 200 on the proximal side of pivot points 216A and 226A, where first and second leg members 212A and 222A transition into first and second proximal end members 232 and 234, respectively. The interfacial region is generally demarcated by a ridge or shoulder 262 from which, in the proximal direction, first and second proximal end members 232 and 234 drop farther into the interior to provide clearance for first arm 312 and second arm 314 of jaw opening member 300 to straddle first and second proximal end members 232 and 234. Ridge 262 can stop forward movement of jaw opening member 300 relative to jaw assembly 200, as described below. In addition, it can be seen that first and second proximal end members 232 and 234 have respective sections of reduced width 264 and 266 just beyond ridge 262 in the proximal direction. From reduced-width sections 264 and 266, first and second proximal end members 232 and 234 taper outwardly, becoming wider in the proximal direction to sections of increased width 268 and 270. By this configuration, first and second fingers 316 and 318 can engage only increased-width sections 268 and 270 of first and second proximal end members 232 and 234, when jaw opening member 300 is positioned rearward relative to jaw assembly 200. If jaw opening member 300 is moved to a more forward position relative to jaw assembly 200 (see, e.g., FIG. 27B), first and second fingers 316 and 318 will be adjacent to reduced-width sections 264 and 266 of first and second proximal end members 232 and 234, at which first and second fingers 316 and 318 do not contact first and second proximal end members 232 and 234 and thus do not affect the width of the jaw aperture. As best shown in FIGS. 28A -28C with respect to second arm 314, respective portions 312A and 314A of first and second arms 312 and 314 can be angled generally outwardly from feeder bar 80 to facilitate the positioning of first and second arms 312 and 314 over first and second proximal ends 232 and 234.

FIG. 27A illustrates the rest position of clip applier 10. This position can correspond to a time just after a clip has been applied to a surgical site and released from jaw assembly 200. The next distal-most clip residing in clip applier 10, clip 78 in FIG. 27A, is positioned in clip channel 72 in preparation to begin the next clip feeding cycle as described hereinabove. At the position shown in FIG. 27A, first and second fingers 316 and 318 of jaw opening member 300 engage first and second proximal ends 232 and 234 of first and second leg members 212A and 222A. By means of the spring action of first and second arms 312 and 314 which is stronger than the jaw spring, first and second fingers 316 and 318 apply respective biasing forces on first and second proximal end members 232 and 234. As a result, first and second proximal end members 232 and 234 are urged generally toward the centerline of clip applier 10 coincident with line B-B. Consequently, on the distal side of pivot points 216A and 226A, first and second leg members 212A and 222A are urged generally outwardly, as generally depicted by the arrows in FIG. 27A, thereby increasing the width of the jaw aperture and improving the ability of an applied clip to be released from jaw assembly 200. Also at this position, as shown in FIG. 28A and in greater detail in FIG. 29A, end portion 324A of tab 324 of jaw opening member 300 extends into tab aperture 325 of feeder bar 80. Hence, as feeder bar 80 is driven forward to contact clip 78 and feed clip 78 into jaw assembly 200, feeder bar 80 can also drive jaw opening member 300 forward.

Figure 26B:
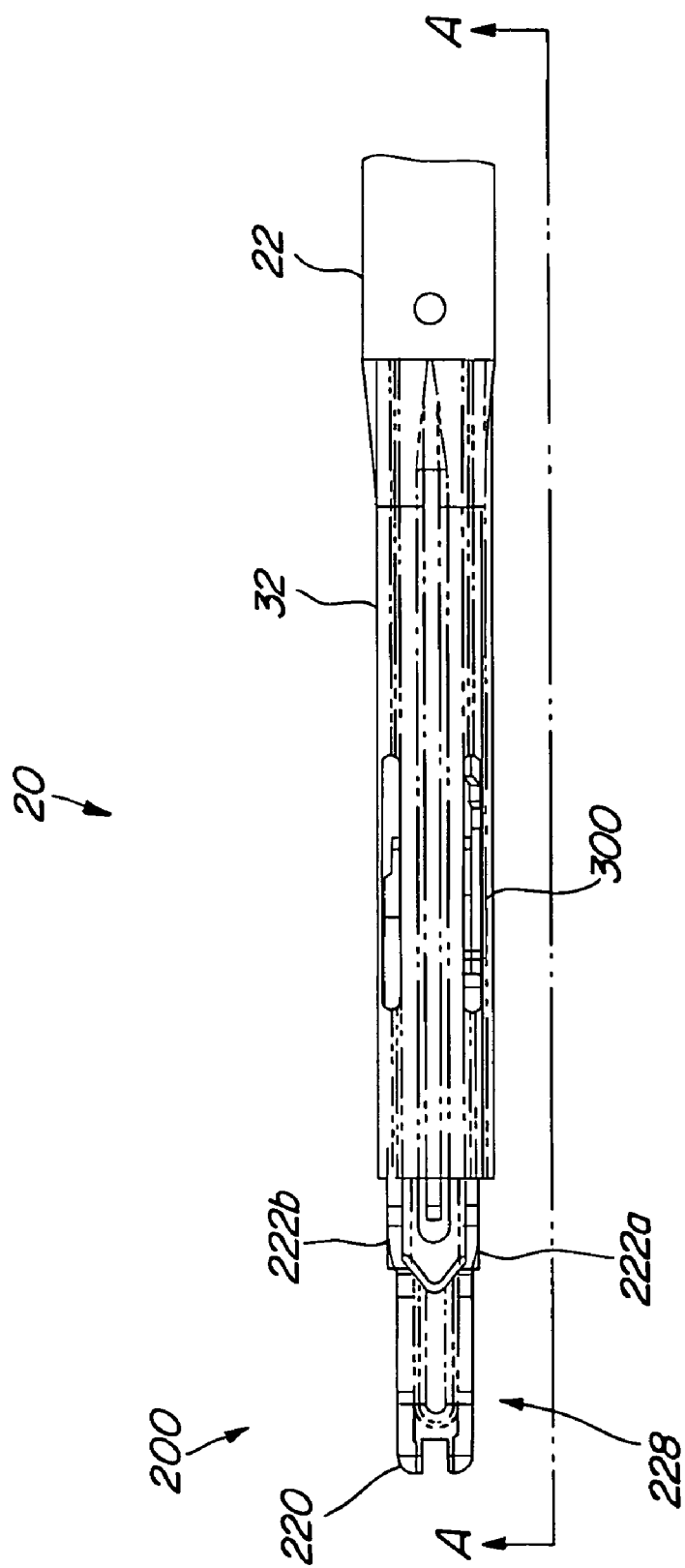
FIG. 26B is a top plan view of the clip applier depicted in FIG. 26A, illustrating the jaw assembly in a jaw set position.
Figure 26C:
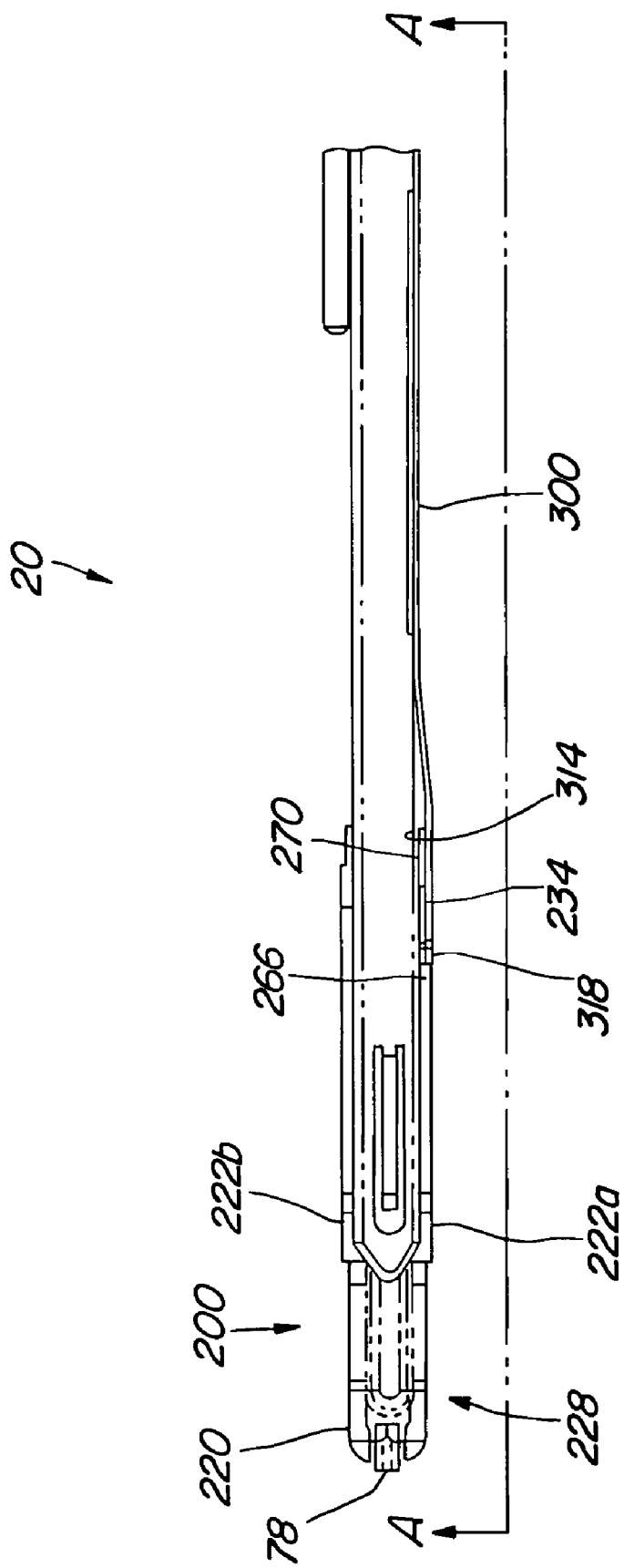
FIG. 26C is a top plan view of the clip applier depicted in FIGS. 26A and 26B, illustrating a clip being fed into the jaw assembly.
Figure 27B:
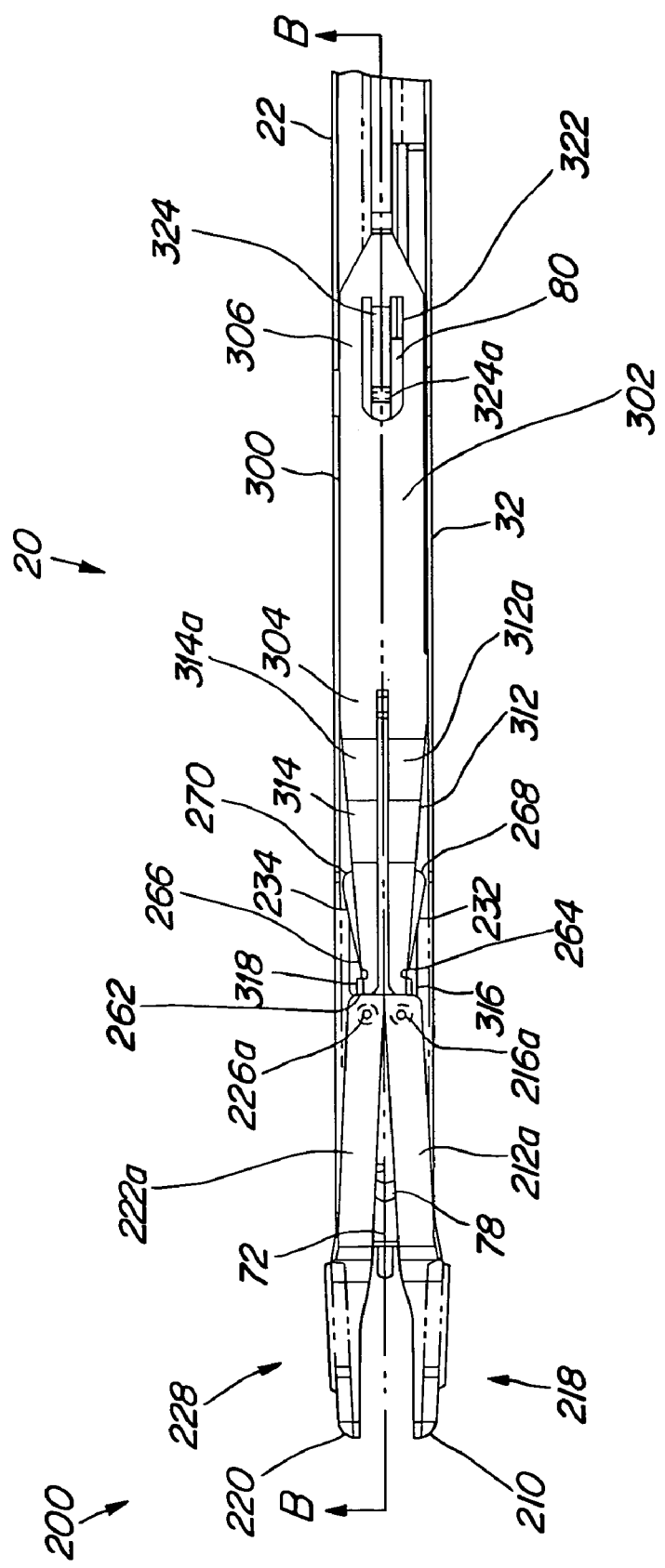
FIG. 27B is a cutaway side elevation view of the clip applier in a position corresponding to that shown in FIG. 26B.
Figure 27C:
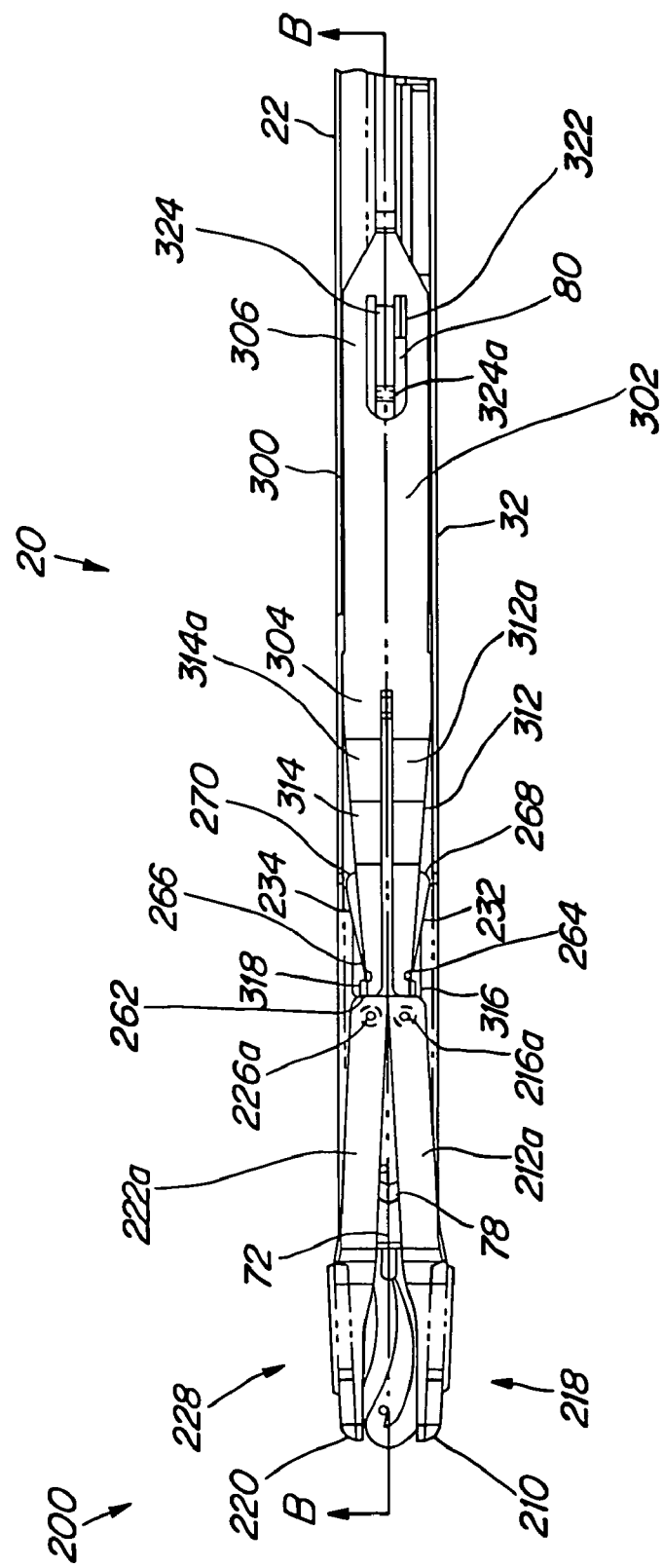
FIG. 27C is a cutaway side elevation view of the clip applier in a position corresponding to that shown in FIG. 26C.

Referring now to FIGS. 26B and 27B, clip applier 10 is operated to actuate jaw assembly 200 into the jaw set position in preparation for feeding clip 78 into jaw assembly 200, as described hereinabove. As feeder bar 80 is driven into engagement with clip 78, feeder bar 80 carries jaw opening member 300 forward as generally depicted by the arrows in each of FIGS. 27B-29B, due to the contact between end portion 324A of tab 324 and tab aperture 325 shown in FIGS. 28B and 29B. As shown in FIG. 27B, the forward movement of jaw opening member 300 is limited by ridge 264 formed by leg members 212A and 222A of jaw assembly 200. Ridge 262 acts as a stop against which first and second fingers 316 and 318 of jaw opening member 300 abut. At this position, first and second fingers 316 and 318 are adjacent to reduced-width sections 264 and 266 of proximal end members 232 and 234 of jaw members 210 and 220. Due to reduced width sections 264 and 266, first and second fingers 316 and 318 reduce the force on end members 232 and 234 and hence to do not operate to increase the jaw aperture. At this position, an increase in the jaw aperture is not desired because, as described previously, the jaw aperture is preferably set at a width that is substantially the same as that of clip channel 72, so as to receive clip 78 in a compressed state that enables a smooth transition of clip 78 from clip channel 72 into jaw assembly 200.

Referring now to FIGS. 26C-28C, clip applier 10 has been further actuated so as to advance clip 78 into jaw assembly 200, as generally depicted by the arrow in FIG. 28C. As shown in FIG. 28C, the advancement of clip 78 is accomplished by driving feeder bar 80 farther in the distal direction. Feeder bar 80 moves forward relative to jaw opening member 300 during this stage of operation. That is, as shown in FIG. 27C, first and second fingers 316 and 318 of jaw opening member 300 remain abutted against ridge 262 of leg members 212A and 222A. As feeder bar 80 moves forward relative to jaw opening member 300, tab aperture 325 (see FIG. 29B) of feeder bar 80 necessarily moves relative to jaw opening member 300 as well. Hence, end portion 324A of tab 324 of jaw opening member 300 is deflected because of angled end 324A out from tab aperture 325 and, as shown in FIG. 29C, remains in contact with a surface of feeder bar 80 as feeder bar 80 and its tab aperture 325 continue to move forward and allowing the feeder bar 80 to move forward and feed the clip.

As described previously, after clip 78 has been fed into jaw assembly 200, the continued forward stroke of clip applier 10 is executed to apply clip 78 to target tissue at the surgical site. Subsequently, clip 78 is fully released from jaw assembly 200 as jaw assembly 200 is opened to full aperture. As described previously with reference to FIG. 27A, the jaw aperture is increased to facilitate the release of clip 78 by the action of jaw opening member 300 in jaw assembly 200. Subsequently, clip applier 10 can be reset during its return stroke as generally described hereinabove. Because tab 324 of jaw opening member 300 is essentially spring loaded and remains in contact with feeder bar 80, as feeder bar 80 moves in the proximal direction during the return stroke, end portion 324A of tab 324 eventually drops back down into tab aperture 325, allowing feeder bar 80 to carry jaw opening member 300 back to the starting position shown in FIGS. 27A and 30.

Referring now to FIG. 30, if jaw assembly 200 is forced closed (as depicted by the arrows) while clip applier 10 is in the reset position, jaw opening member 300 is configured so as to allow such closure. Although jaw opening member 300 has been reset to a position at which its first and second fingers 316 and 318 respectively engage first and second proximal end members 232 and 234 of first and second jaw members 210 and 220, first and second arms 312 and 314 of jaw opening member 300 act as springs and thus flex in response to the outward movement of proximal end members 232 and 234 that accompanies the closing of jaw assembly 200.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. An apparatus for applying surgical clips, comprising:
   (a) a jaw assembly comprising first and second opposing jaw members, each jaw member including: a first and a second opposing leg member connected by a bridge member at a proximal end of the first and second opposing leg members, a first and a second opposing arm member connected to a distal end of the first and second opposing leg members, each leg member having an outer cam surface; wherein the first and second jaw members define a variable jaw aperture therebetween for receiving a clip, the first and second jaw members pivotable for varying a width of the jaw aperture; and
   (b) a jaw opening member comprising a distal portion generally adjacent to the first and second jaw members, the distal portion movable into engagement with the first and second jaw members for increasing the width of the jaw aperture,
   wherein the first and second jaw members are pivotable about respective first and second pivot points and comprise respective first and second end members, the first and second end members are disposed opposite to the jaw aperture relative to the first and second pivot points, and the distal portion is movable into engagement with the first and second end members for increasing the width of the jaw aperture,
   and further wherein the first and second end members comprise respective first and
   second reduced-width sections and first and second increased-width sections, the distal
   portion is axially movable relative to the jaw assembly between a first position and a
   second position, the distal portion at the first position engages the increased-width
   sections for increasing the width of the jaw aperture, and the distal portion at the
   second position is adjacent to the reduced-width sections in non-operatively contacting relation therewith so as not to affect the width of the jaw aperture.

2. The apparatus according to claim 1 wherein the first and second jaw members form a ridge against which the jaw opening member is abuttable for limiting movement of the jaw opening member in an axial direction toward the jaw assembly.

3. The apparatus according to claim 1 wherein the first and second jaw members comprise respective first and second leg members adjoining the first and second end members generally at the first and second pivot points.

4. The apparatus according to claim 1 wherein the first and second jaw members are arranged on either side of a central axis, and the distal portion is movable into engagement with the first and second end members for pivoting the first and second end members toward the central axis.

5. The apparatus according to claim 4 wherein the first and second leg members adjoin the first and second end members generally at the first and second pivot points, and pivoting of the first and second end members toward the central axis corresponds to pivoting of the first and second leg members away from the central axis.

6. The apparatus according to claim 1 comprising an elongate assembly, wherein the first and second jaw members are pivotably coupled to the elongate assembly.

7. The apparatus according to claim 6 wherein the elongate assembly comprises a channel for containing clips, the first and second jaw members are pivotably coupled to the channel, and the jaw opening member is movable relative to the channel.

8. The apparatus according to claim 7 wherein the elongate assembly comprises a generally hollow elongate member, and the channel and jaw opening member are disposed in the elongate member.

9. The apparatus according to claim 6 wherein the jaw opening member includes a key which engages a slot on the elongate assembly.

10. The apparatus according to claim 1 comprising an elongate member movable into engagement with the first and second jaw members for pivotably decreasing the width of the jaw aperture.

11. The apparatus according to claim 10 wherein the elongate member has an interior and the jaw opening member is movably disposed in the interior.

12. Apparatus according to claim 1 comprising a feeding device axially movable toward the jaw aperture for feeding a clip therein, wherein the jaw opening member is engageable with the feeding device for movement therewith.

13. The apparatus according to claim 12 wherein the jaw opening member comprises a tab biased toward the feeding device, the feeding device has a hole, and the tab is removably extendable into the hole.

14. The apparatus according to claim 1 further comprising a hook at a distal end of each arm member.

15. The apparatus according to claim 1 further comprising a first guide which clips over the first arm of the first jaw member and the first arm of the second jaw member and a second guide which clips over the second arm of the first jaw member and the second arm of the second jaw member.

16. The apparatus according to claim 1 further comprising a jaw closing collar having inner cam surfaces, the jaw closing collar being slideable from a first position to a second position.

17. The apparatus according to claim 16 wherein at the first position, the jaw closing collar is disengaged with the first and second jaw members.

18. The apparatus according to claim 16 wherein at the second position, the jaw closing collar is engaged with the first and second jaw members such that the inner cam surfaces of the collar contact the outer cam surfaces of each jaw member.

19. An apparatus for applying surgical clips, comprising:
(a) a jaw assembly comprising first and second opposing jaw members, each jaw member including: a first and a second opposing leg member connected by a bridge member at a proximal end of the first and a second opposing leg members, each leg member having an outer cam surface; wherein the first and second jaw members define a variable jaw aperture therebetween for receiving a clip, the first and second jaw members pivotable about respective first and second pivot points and comprising respective first and second outer surfaces;
(b) an elongate member movable into contact with the first and second outer surfaces for pivotably decreasing a width of the jaw aperture; and
(c) a jaw opening member comprising first and second arms respectively engageable with the first and second outer surfaces for pivotably increasing the width of the jaw aperture,
wherein the first and second jaw members comprise respective first and second end members disposed opposite to the jaw aperture relative to the first and second pivot points, and the first and second arms are movable into engagement with the respective first and second outer surfaces at the first and second end members for increasing the width of the jaw aperture,
wherein the first and second end members comprise respective first and second reduced-width sections and first and second increased-width sections, the first and second arms are axially movable relative to the jaw assembly between a first position and a second position, the first and second arms at the first position respectively engage the first and second outer surfaces at the increased-width sections for increasing the width of the jaw aperture, and the first and second arms at the second position are spaced away from the first and second outer surfaces at the reduced-width sections so as not to affect the width of the jaw aperture.

20. The apparatus according to 19 wherein the first and second jaw members form a ridge generally axially between the first and second pivot points and the first and second end members, and the first and second arms are abuttable against the ridge for limiting movement of the jaw opening member in an axial direction toward the jaw assembly.

21. The apparatus according to claim 19 comprising an elongate assembly, wherein the first and second jaw members are pivotably coupled to the elongate assembly at the respective first and second pivot points and the jaw opening member is movably disposed in the elongate assembly.

22. The apparatus according to claim 19 comprising a feeding device axially movable toward the jaw aperture for feeding a clip therein, wherein the jaw opening member is engageable with the feeding device for movement therewith.

23. The apparatus according to claim 19 wherein the first and second arms are generally adjacent to the first and second jaw members, and comprise respective first and second extensions oriented at an angle relative to the first and second arms for engaging the respective first and second outer surfaces.

24. An apparatus for applying surgical clips, comprising:
(a) a jaw assembly comprising first and second opposing jaw members, each jaw member including: a first and a second opposing leg member connected by a bridge member at a proximal end of the first and second opposing leg members, a first and a second opposing arm member connected to a distal end of the first and second opposing leg members, each leg member having an outer cam surface; wherein the first and second jaw members define a variable jaw aperture therebetween for receiving a clip, the first and second jaw members pivotable for varying a width of the jaw aperture; and (b) a feeding device axially movable toward the jaw aperture for feeding a clip therein; and
(c) a jaw opening member engageable with the feeding device for movement therewith and movable into engagement with the first and second jaw members for increasing the width of the jaw aperture;
wherein the first and second jaw members are pivotable about respective first and second pivot points and comprise respective first and second end members, the
first and second end members are disposed opposite to the jaw aperture relative to the first and second pivot points, and the jaw opening member is movable into engagement with the first and second end members for increasing the width of the jaw aperture, and further wherein the first and second end members comprise respective first and second reduced-width sections and first and second increased-width sections, the distal portion is axially movable relative to the jaw assembly between a first position and a second position, the jaw opening member at the first position engages the increased width sections for increasing the width of the jaw aperture, and the jaw opening member at the second position is adjacent to the reduced-width sections in non-operatively contacting relation therewith so as not to affect the width of the jaw aperture.

25. The apparatus according to claim 24 comprising an elongate assembly, wherein the first and second jaw members are pivotably coupled to the elongate assembly, and the feeding device and jaw opening member are movably disposed in the elongate assembly.

26. The apparatus according to claim 25 wherein the elongate assembly comprises a channel for containing clips, the first and second jaw members are pivotably coupled to the channel, and the feeding device and jaw opening member are movable relative to the channel.

27. The apparatus according to claim 24 wherein the elongate assembly comprises an elongate member movable into contact with the first and second jaw members for pivotably decreasing the width of the jaw aperture.

28. The apparatus according to claim 24 wherein the jaw opening member comprises a proximal portion engageable with the feeding device.

29. The apparatus according to claim 28 wherein the proximal portion comprises a tab biased toward the feeding device, the feeding device has a hole, and the tab is removably extendable into the hole.

* * * * *

UNITED STATES PATENT AND TRADEMARK OFFICE
CERTIFICATE OF CORRECTION

PATENT NO.        : 7,585,304 B2                                    Page 1 of 1
APPLICATION NO.   : 10/770299
DATED             : September 8, 2009
INVENTOR(S)       : J. David Hughett It is certified that error appears in the above-identified patent and that said Letters Patent is hereby corrected as shown below:

Column 17, claim 3, please replace "The apparatus according to claim 1 wherein the first and second jaw members comprise respective first and second leg members adjoining the first and second end members generally at the first and second pivot points" with --The apparatus according to claim 1 wherein the first and second leg members adjoin the first and second end members generally at the first and second pivot points--;

Column 18, claim 20, line 1, please replace "to 19" with --to claim 19--.

Signed and Sealed this

Twentieth Day of October, 2009

David J. Kappos
*Director of the United States Patent and Trademark Office*